(12) United States Patent
Plos

(10) Patent No.: US 7,585,332 B2
(45) Date of Patent: Sep. 8, 2009

(54) COMPOSITION CONTAINING A STYRYL OR IMINE TYPE DYE AND A THIOL COMPOUND, HAIR COLORING PROCESS AND DEVICE

(75) Inventor: Grégory Plos, Tokyo (JP)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 11/907,622

(22) Filed: Oct. 15, 2007

(65) Prior Publication Data

US 2009/0019645 A1    Jan. 22, 2009

Related U.S. Application Data

(60) Provisional application No. 60/853,754, filed on Oct. 24, 2006.

(30) Foreign Application Priority Data

Oct. 13, 2006    (FR)  .................................. 06 54260

(51) Int. Cl.
*A61Q 5/10* (2006.01)

(52) U.S. Cl. .................. 8/405; 8/426; 8/565; 8/566; 8/567; 8/568; 8/570; 8/571; 8/574; 8/575; 8/576; 8/585; 8/586; 8/587

(58) Field of Classification Search .................. 8/426, 8/565, 566, 567, 568, 570, 571, 574, 575, 8/576, 585, 586, 587, 405

See application file for complete search history.

(56) References Cited

U.S. PATENT DOCUMENTS

| | | | |
|---|---|---|---|
| 4,003,633 A | 1/1977 | Yamashita | |
| 4,139,274 A | 2/1979 | Yamashita et al. | |
| 4,147,862 A | 4/1979 | Hayami et al. | |
| 4,314,058 A * | 2/1982 | Hayami et al. | ............... 544/89 |
| 4,340,624 A | 7/1982 | Yamashita et al. | |
| 4,380,629 A * | 4/1983 | Yamashita et al. | .......... 548/217 |
| 7,399,319 B2 | 7/2008 | Plos | |
| 2006/0182697 A1 | 8/2006 | Lalleman et al. | |
| 2008/0189878 A1 | 8/2008 | Plos | |

FOREIGN PATENT DOCUMENTS

| | | |
|---|---|---|
| DE | 2 541 665 | 4/1976 |
| EP | 1 747 774 | 1/2007 |
| FR | 2 285 438 | 4/1976 |
| FR | 2 285 439 | 4/1976 |
| FR | 2 293 024 | 6/1976 |
| FR | 2 888 747 | 1/2007 |
| JP | 55-031057 | 3/1980 |
| JP | 55-113710 | 9/1980 |
| JP | 56-025106 | 3/1981 |
| JP | 56-081522 | 7/1981 |
| JP | 56-150006 | 11/1981 |
| JP | 56-161489 | 12/1981 |
| JP | 57-041652 | 1/1982 |
| JP | 58-048031 | 3/1983 |
| JP | 59-121319 | 7/1984 |
| JP | 59-052193 | 12/1984 |
| JP | 60-057320 | 4/1985 |
| JP | 60-057322 | 4/1985 |
| JP | 60-057323 | 4/1985 |
| JP | 60-200233 | 10/1985 |
| JP | 61-121040 | 6/1986 |
| JP | 61-147235 | 7/1986 |
| JP | 63-280727 | 11/1988 |
| JP | 02-179618 | 7/1990 |
| JP | 08-222268 | 8/1996 |
| JP | 10-114151 | 5/1998 |
| JP | 11-034489 | 2/1999 |
| JP | 11-034497 | 2/1999 |
| JP | 2000-292817 | 10/2000 |
| JP | 2001-081342 | 3/2001 |
| JP | 2001-109021 | 4/2001 |
| JP | 2001-246862 | 9/2001 |
| JP | 2003-315839 | 11/2003 |

OTHER PUBLICATIONS

"Sciences des traitements capillaires" by Charles Zviak, 1988, published by Masson, pp. 215 and 278.
Biochemistry text by J. H. Weil, 1983, p. 5 et seq.
Biochemistry text by L. Stryer, 1995, p. 22.
Biochemistry text by A. Lehninger, 1993, pp. 115-116.
Biochemistry text by D. Boeck-Wesmael, 1994, pp. 57-59.
French Search Report issued in French Patent Application No. FR 0 654 259. (2007).
French Search Report issued in French Patent Application No. FR 0 654 260. (2007).
International Search Report issued in International Patent Application No. PCT/FR2007/052129. (2008).
International Search Report issued in International Patent Application No. PCT/FR2007/052130. (2008).
Amendment Under 37 C.F.R. § 114 filed in co-pending U.S. Appl. No. 11/907,525. (2007).

* cited by examiner

*Primary Examiner*—Eisa B Elhilo
(74) *Attorney, Agent, or Firm*—Finnegan, Henderson, Farabow, Garrett & Dunner, LLP

(57) ABSTRACT

The present invention relates to compositions for dyeing keratin fibers, and in particular human keratin fibers such as the hair, comprising at least one compound of styryl or imine type containing a heterocycle and at least one thiol compound. The present invention makes it possible in particular to obtain a chromatic and fast coloration of keratin fibers, especially with respect to shampooing. Moreover, the color obtained is visible even on dark hair without necessarily using an oxidizing composition. The invention also makes it possible to obtain a coloration which, under certain conditions, does not stain.

31 Claims, No Drawings

COMPOSITION CONTAINING A STYRYL OR IMINE TYPE DYE AND A THIOL COMPOUND, HAIR COLORING PROCESS AND DEVICE

CROSS-REFERENCE TO RELATED APPLICATIONS

This application claims benefit of priority under 35 U.S.C. § 119 to French Patent Application No. 0654260, filed Oct. 13, 2006, and the benefit of U.S. Provisional Application No. 60/853,754, filed Oct. 24, 2006, the content of all of which is incorporated herein by reference.

The present invention relates to a composition for dyeing keratin fibers, and in particular human keratin fibers such as the hair, comprising at least one dye of styryl or imine type and at least one thiol compound of weak acid type. The invention furthermore relates to a dyeing process using a composition of this type, and to a device suitable for implementing said process.

It is known practice to dye keratin fibers, and in particular human keratin fibers such as the hair, with compositions containing oxidation dye precursors, which are generally known as oxidation bases, such as ortho- or para-phenylenediamines, ortho- or para-aminophenols and heterocyclic compounds such as diaminopyrazole derivatives. These oxidation bases are colorless or weakly colored compounds, which, when combined with oxidizing products, give rise to colored compounds via a process of oxidative condensation.

It is also known that the shades obtained with these oxidation bases can be varied by combining them with couplers or coloration modifiers, the latter being chosen especially from aromatic meta-diamines, meta-aminophenols, meta-diphenols and certain heterocyclic compounds such as indole compounds.

Another advantage of this type of dyeing is that it is visible on dark hair. Effectively, since the oxidative process is performed in alkaline medium, generally in the presence of aqueous ammonia, the bleaching of melanin, the natural pigment of keratin fibers and especially of the hair, takes place in parallel with the condensation of the dye precursors. The color obtained may thus also be visible even on dark hair.

The colorations obtained show good fastness especially with respect to shampooing. However, chromatic colorations are rarely obtained via this method.

It is also known practice to dye keratin fibers with compositions containing direct dyes. These compounds are colored and coloring molecules with affinity for keratin fibers. They are applied to the keratin fibers for a time necessary to obtain the desired coloration, and are then generally rinsed out.

The standard direct dyes used are in particular dyes of the nitrobenzene, anthraquinone, nitropyridine, azo, cationic azo, xanthene, acridine, azine or triarylmethane type or natural dyes.

It is possible to obtain colorations lighter than those of the hair before dyeing, if the direct dyeing is performed in the presence of an oxidizing agent. This is then referred to as direct dyeing under lightening conditions.

Direct dyeing advantageously makes it possible to achieve very chromatic colors, but they always have the drawback of being temporary or semipermanent. Specifically, the fastness of direct dyes on the hair remains limited, which leads to fading of the color, or even changing of the color over time, due to one or more of the dyes used at the start.

One drawback of these two dyeing modes is the need to use an oxidizing composition for the oxidation dyeing or to obtain lightened direct dyeing. However, it is known that oxidizing compositions cause, in the long run, degradation of hair fibers.

Another drawback of these dyeing modes lies in the fact that these compositions are initially colored, as in the case of compositions using direct dyes, or else they become colored during the application, as is the case for compositions comprising one or more oxidation dye precursors. Consequently, direct dyeing and oxidation dyeing have the drawback of being soiling.

French patent application FR 05 52277 has recently described the use of compounds of styryl or imine type existing in a colored form and in an uncolored form, for dyeing keratin fibers. Thus, under certain conditions, the composition used is colorless or weakly colored and the color is revealed in the keratin fibers once the composition has been applied, which makes it possible to solve the problem of staining of the skin and of the fabrics used.

Although these compositions afford numerous advantages over the existing compositions, while at the same time offering satisfactory dyeing efficacy, it nevertheless remains that it may be desired to further increase the uptake and to reduce the selectivity of the colorations obtained.

The present invention furthermore allows access to keratin fiber colorations that are lighter than the initial color, without necessarily using an oxidizing composition.

Finally, the process according to the invention makes it possible, under certain conditions, to afford a process that does not stain.

These aims and others are achieved by the present invention, one subject of which is a composition for dyeing keratin fibers, comprising, in a suitable dyeing medium, a) at least one compound of formula (I), and the addition salts thereof:

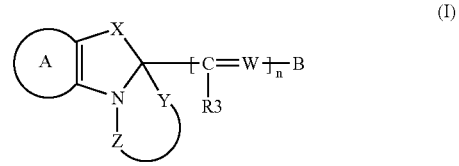

(I)

in which:
A is a substituted or unsubstituted, 5- to 16-membered, fused or non-fused aromatic or heteroaromatic nucleus;
X represents an oxygen atom, a sulfur atom or a group $CR_1R_2$;
$R_1$ and $R_2$ represent, independently of each other, a hydrogen atom, a $C_1$-$C_6$ alkyl radical, a $C_1$-$C_6$ hydroxyalkyl radical, a $C_1$-$C_6$ alkoxyalkyl radical or an alkylene chain that may contain an oxygen or sulfur atom; $R_1$ and $R_2$ may together form an aromatic or non-aromatic 5- or 6-membered ring optionally containing one or more heteroatoms such as a nitrogen, oxygen or sulfur atom;
$R_3$ represents a hydrogen atom, a halogen atom, a $C_1$-$C_6$ alkyl radical, a cyano radical, an aromatic group, a phenoxy group or a nitro radical;
W represents a group $CR_4$ or a nitrogen atom;
$R_4$ represents a hydrogen atom, a halogen atom, a $C_1$-$C_6$ alkyl radical, a cyano radical, an aromatic group, a phenoxy radical or a nitro radical.
Y represents an oxygen atom, a sulfur atom or a group $NR_5$;
$R_5$ represents a hydrogen atom or a $C_1$-$C_6$ alkyl radical;

Z represents a group —$C_pH_{2p}$—, with p being an integer between 2 and 4, which may be unsubstituted or substituted with one or more substituents chosen from halo, hydroxyl, alkyl, haloalkyl, alkoxy, amino, mono- or dialkylamino, mono- or dihydroxyalkylamino and carboxyl radicals; a group —$C_qH_{2q}CO$—, with q being an integer between 1 and 3, which may be unsubstituted or substituted with one or more substituents chosen from halo, hydroxyl, alkyl, haloalkyl, alkoxy, amino, mono- or dialkylamino, mono- or dihydroxyalkylamino and carboxyl radicals;

n represents an integer from 1 to 4;

B represents a substituted or unsubstituted, 5- to 16-membered, fused or non-fused aromatic or heteroaromatic nucleus, and b), at least one thiol compound comprising at least one thiol function (SH) and a saturated or unsaturated group containing from 1 to 20 carbon atoms, the said group being optionally interrupted with one or more non-adjacent groups (separated by at least one carbon atom) chosen from —O—, —S—, —S—S—, amino (—NR—), carbonyl (—CO—), oxycarbonyl (—O—CO—), aminocarbonyl (—NR—CO—), aromatic or heteroaromatic nucleus, the amino groups being unsubstituted or substituted with one or two $C_1$-$C_6$ alkyl radicals; on condition that the sulfur atom of the thiol function is attached to the said group by means of a carbon atom; the said group being optionally substituted with one or more hydroxyl, $C_1$-$C_6$ alkoxy, hydroxycarbonyl, ($C_1$-$C_6$) alkoxycarbonyl, amino, aminocarbonyl or alkylcarbonylamino, in which the amino function is unsubstituted or substituted with one or two $C_1$-$C_6$ alkyl radicals.

A subject of the present invention is also a process for dyeing keratin fibres using such a composition.

Another subject of the invention is a multi-compartment device for implementing the dyeing process in accordance with the invention.

The invention makes it possible in particular to obtain a keratin fiber coloration that is chromatic and fast, especially with respect to shampooing.

As indicated previously, another advantage of the invention is that of providing a clean method of coloration, in other words a method that does not stain.

Specifically, under certain conditions of implementation of the invention, the compound applied to the keratin fibers is colorless or weakly colored and the coloration is not revealed until later, once the compound has been applied to the keratin fibers.

The revelation of the coloration is performed by opening the heterocycle to lead to species of formula (I') below, which are colored:

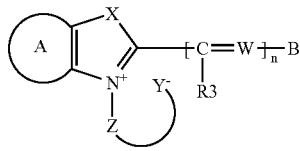

A, X, Z, W, R3 and n having the same meanings as those indicated previously.

The opening of the heterocycle formed by N, Y and Z in the dye compounds of formula (I) may be performed under the effect of a stimulus such as light, an electrical current, heat, the addition of an acidifying agent, the addition of solvent or an electromagnetic radiation.

The composition applied to the keratin fibers is thus substantially colorless, and transparent or nontransparent, as are the rinsing waters or the shampoo-rinsing waters. Thus, the application of the composition according to the invention may be nonsoiling.

Moreover, it is possible to efface the color obtained. It suffices in point of fact to treat the keratin fibers, colored with the composition according to the invention, with a composition whose role will be to increase the pH of the fibers above the pKa of the dyes of formula (I) present on and in the fibers. The open heterocycles of the compounds of formula (I') will reclose to once again give the compounds of formula (I).

Finally, it has been found that the application of the composition to dark hair, more particularly characterized by a tone depth of less than or equal to 6, leads to an increase in the tone depth of the coloration by at least one tone, which corresponds to visible lightening of the fiber, without the need to use an oxidizing composition.

In the context of the present invention, the term "heteroaromatic nucleus" means an aromatic nucleus comprising one or more heteroatoms such as nitrogen, sulfur, oxygen or phosphorus atoms.

In the context of the present invention, the term "fused" means at least two conjoined rings with at least two atoms in common.

A halo radical denotes a halogen atom chosen from chlorine, bromine, iodine and fluorine.

The term "alkyl radical" (alk) means a linear or branched radical, for example a methyl, ethyl, n-propyl, isopropyl, n-butyl or tert-butyl radical. An alkoxy radical is an alk-O— radical, a mono- or dialkylamino radical is a radical —N(alk)$_n$ with n=1 or 2, an alkylcarbonyl radical is an alk-CO— radical, an alkoxycarbonyl radical is an alk-O—CO— radical and an alkylcarbonylalkyl radical is an alk-CO-alk- radical, in each of these definitions the alkyl radical being as defined above.

A substituted alkyl radical is a monosubstituted or polysubstituted alkyl. For example, a hydroxyalkyl or an aminoalkyl is an alkyl that may be substituted with one or more hydroxyl or amino groups.

The term "aryl radical" (ar) means a carbon-based radical derived from fused or non-fused benzene compounds, for example phenyl, anthracenyl or naphthyl.

Examples of aromatic or non-aromatic 5- or 6-membered rings that may be mentioned include 1,3-cyclopentadiene, benzene, cyclopentane and cyclobutane.

The compounds of formula (I) may be neutralized with an anionic or cationic counterion when they bear a charge. The negative counterions may be chosen, for example, from a halide such as a chloride, bromide, iodide or fluoride, perchlorate, p-methylbenzenesulfonate, tetrafluoroborate, sulfate, alkyl sulfate, toluenesulfonate or sulfonate. The cationic counterions may be chosen from the cations derived from alkali metal and alkaline-earth metal salts, such as sodium or potassium ions.

In the context of the present invention, the term "dark hair" means hair whose tone depth is less than or equal to 6 (dark blond) and preferably less than or equal to 4 (chestnut).

It is recalled that the lightening of the hair is evaluated by the "tone depth", which characterizes the degree or level of lightening. The notion of "tone" is based on the classification of natural shades, one tone separating each shade from the one immediately following or preceding it. This definition and the classification of natural shades are well known to hairstyling professionals and are published in the book "Sciences des traitements capillaires" by Charles Zviak, 1988, published by Masson, pp. 215 and 278. The tone depths range from 1 (black) to 10 (light blond), one unit corresponding to one tone; the higher the figure, the lighter the shade.

According to one particular embodiment of the invention, A is a benzene, anthracene, naphthalene or quinoline nucleus.

According to one particular embodiment of the invention, A is unsubstituted or substituted with one or more groups that may be chosen from a halo radical, a $C_1$-$C_6$ alkyl radical, a $C_1$-$C_6$ alkoxy radical, a $C_1$-$C_6$ alkylsulfonyl radical (—$SO_2$-alkyl), a $C_1$-$C_6$ alkylsulfonate radical (—$SO_3$-alkyl), a cyano radical, a trifluoromethyl radical, a $C_1$-$C_6$ alkylcarbonyl radical, a trifluoromethylsulfonyl radical (—$SO_2$—$CF_3$), a trifluoromethylcarbonyl radical, a phenylsulfonyl radical (—$SO_2$-Ph), a phenylsulfonate radical (—$SO_3$-Ph), a phenylcarbonyl radical, a nitro radical, a $C_1$-$C_6$ alkoxycarbonyl radical, a phosphonyl radical (—$PO(OH)_2$), a phosphonyl($C_1$-$C_6$)alkyl radical (-alkyl-$PO(OH)_2$), a hydroxyl radical, an amino radical, a di($C_1$-$C_6$)alkylamino radical, a (hydroxy($C_1$-$C_6$)alkyl)amino radical, a di(hydroxy($C_1$-$C_6$)alkyl)amino radical, an (amino($C_1$-$C_6$)alkyl)amino radical, a di(amino($C_1$-$C_6$)-alkyl)amino radical, a (hydroxy($C_1$-$C_6$)alkyl) (($C_1$-$C_6$)-alkyl)amino radical, an (amino($C_1$-$C_6$)alkyl) (($C_1$-$C_6$)-alkyl)amino radical, an (amino($C_1$-$C_6$)alkyl) (hydroxy-($C_1$-$C_6$)alkyl)amino radical, a hydroxy($C_1$-$C_6$)alkyl radical, an amino($C_1$-$C_6$)alkyl radical, a (($C_1$-$C_6$)alkyl)amino($C_1$-$C_6$) alkyl radical, a di(($C_1$-$C_6$)alkyl)-amino($C_1$-$C_6$)alkyl radical, a (hydroxy($C_1$-$C_6$)alkyl)amino-($C_1$-$C_6$)alkyl radical, a di(hydroxy($C_1$-$C_6$)alkyl)amino-($C_1$-$C_6$)alkyl radical, an (amino($C_1$-$C_6$)alkyl)amino($C_1$-$C_6$)-alkyl radical, a di(amino($C_1$-$C_6$)alkyl)amino($C_1$-$C_6$)alkyl radical, a (($C_1$-$C_6$)alkyl) (hydroxy($C_1$-$C_6$)alkyl)amino-($C_1$-$C_6$)alkyl radical, an (amino($C_1$-$C_6$) alkyl) (($C_1$-$C_6$)-alkyl)amino radical, a (hydroxy($C_1$-$C_6$) alkyl) (($C_1$-$C_6$)-alkyl)amino ($C_1$-$C_6$) alkyl radical; a phenyl ($C_1$-$C_6$) alkyl radical optionally substituted with one or more substituents chosen from halo, hydroxyl, alkyl, haloalkyl, alkoxy, amino, mono- or dialkylamino, mono- or dihydroxyalkylamino and carboxyl radicals, a cationic group of the quaternary ammonium type, a $C_1$-$C_6$ alkyl radical substituted with a cationic group of the quaternary ammonium type, a carboxyl radical, a ($C_1$-$C_6$)alkyl radical substituted with a carboxyl radical, a thio radical, a thio($C_1$-$C_6$)alkyl radical, a sulfonate radical (—$SO_3^-$), a ($C_1$-$C_6$)alkyl radical substituted with a sulfonate radical, a ($C_1$-$C_6$)alkylcarbonyl($C_1$-$C_6$)alkyl radical, a di(halo($C_1$-$C_6$)alkyl)amino radical, an acetamido radical, an aryloxy radical, an aryloxy-($C_1$-$C_6$)alkyl radical, an ethenyl radical (—CH═$CH_2$), an ethenylcarbonyl radical (—CO—CH═$CH_2$); two adjacent groups possibly forming an aromatic or heteroaromatic ring, which is unsubstituted or substituted with one or more substituents chosen from halo, hydroxyl, alkyl, haloalkyl, alkoxy, amino, mono- or dialkylamino, mono- or dihydroxyalkylamino and carboxyl radicals, or a ring of —O—$C_mH_{2m}$—O— type where m is an integer equal to 1 or 2. Preferably, A is unsubstituted or substituted with one or more groups chosen from a ($C_1$-$C_6$) alkylsulfonyl radical; a pyridinium or imidazolium group, which is unsubstituted or substituted with one or more substituents chosen from halo, hydroxyl, alkyl, haloalkyl, alkoxy, amino, mono- or dialkylamino, mono- or dihydroxyalkylamino and carboxyl radicals; a tri-($C_1$-$C_6$)alkylammonium group; a sulfonate radical. By way of example, A may be substituted with a methylsulfonyl radical; a 1-methyl-2-pyridinium group; an imidazolium group; a trimethylammonium group; a sulfonate radical.

According to one particular embodiment of the invention, X is chosen from a group $CR_1R_2$.

According to one particular embodiment of the invention, $R_1$ and $R_2$ are chosen from a $C_1$-$C_6$ alkyl radical. By way of example, $R_1$ and $R_2$ may be a methyl radical; an ethyl radical.

According to one particular embodiment of the invention, $R_3$ is chosen from a hydrogen atom.

According to one particular embodiment of the invention, W is chosen from a group $CR_4$.

According to one particular embodiment of the invention, $R_4$ is chosen from a hydrogen atom.

According to one particular embodiment of the invention, Y is chosen from an oxygen atom or a sulfur atom.

According to one particular embodiment of the invention, Z is chosen from a —$C_pH_{2p}$— group, with p being an integer between 2 and 4, which is unsubstituted or substituted with one or more substituents chosen from halo, hydroxyl, alkyl, haloalkyl, alkoxy, amino, mono- or dialkylamino, mono- or dihydroxyalkylamino and carboxyl radicals. By way of example, Z may be a —$C_2H_4$— group.

According to one particular embodiment of the invention, n is equal to 1 or 2.

According to one particular embodiment of the invention, B is a benzene, carbazole or indole nucleus.

According to one particular embodiment of the invention, B is unsubstituted or substituted with one or more groups that may be chosen from a halo radical, a $C_1$-$C_6$ alkyl radical, a $C_1$-$C_6$ alkoxy radical, a cyano radical, a trifluoromethyl radical, a $C_1$-$C_6$ alkyl-carbonyl radical, a trifluoromethylsulfonyl radical, a trifluoromethylcarbonyl radical, a phenylsulfonyl radical, a phenylcarbonyl radical, a phenyl radical which is unsubstituted or substituted with one or more substituents chosen from halo, hydroxyl, alkyl, haloalkyl, alkoxy, amino, mono- or dialkylamino, mono- or dihydroxyalkylamino and carboxyl radicals, an acylamino radical, a hydroxyl radical, an amino radical, a di(($C_1$-$C_6$)alkyl)amino radical, a hydroxy-($C_1$-$C_6$)alkylamino radical, a di(hydroxy($C_1$-$C_6$) alkyl)amino radical, an (amino($C_1$-$C_6$)alkyl)amino radical, a di(amino($C_1$-$C_6$)alkyl)amino radical, a (($C_1$-$C_6$)alkyl)-(hydroxy($C_1$-$C_6$)alkyl)amino radical, an (amino($C_1$-$C_6$)-alkyl) (($C_1$-$C_6$)alkyl)amino radical, an (amino($C_1$-$C_6$)-alkyl) (hydroxy($C_1$-$C_6$)alkyl)amino radical, a hydroxy-($C_1$-$C_6$)alkyl radical, an amino($C_1$-$C_6$)alkyl radical, a ($C_1$-$C_6$)alkylamino ($C_1$-$C_6$)alkyl radical, a di(($C_1$-$C_6$)-alkyl)amino($C_1$-$C_6$)alkyl radical, a (hydroxy($C_1$-$C_6$)-alkyl)amino($C_1$-$C_6$)alkyl radical, a di(hydroxy($C_1$-$C_6$)-alkyl)amino($C_1$-$C_6$)alkyl radical, an amino($C_1$-$C_6$)-alkylamino($C_1$-$C_6$)alkyl radical, a di(amino ($C_1$-$C_6$)-alkyl)amino($C_1$-$C_6$)alkyl radical, a (($C_1$-$C_6$)alkyl) (hydroxy($C_1$-$C_6$)alkyl)amino($C_1$-$C_6$)alkyl radical, a (($C_1$-$C_6$) alkyl) (amino($C_1$-$C_6$)alkyl)amino radical, a (hydroxy($C_1$-$C_6$) alkyl) (($C_1$-$C_6$)alkyl)amino($C_1$-$C_6$) alkyl radical, a phenyl ($C_1$-$C_6$)alkyl radical which is unsubstituted or substituted with one or more substituents chosen from halo, hydroxyl, alkyl, haloalkyl, alkoxy, amino, mono- or dialkylamino, mono- or dihydroxyalkylamino and carboxyl radicals, a cationic group of the quaternary ammonium type, a ($C_1$-$C_6$)alkyl radical substituted with a cationic group of the quaternary ammonium type, a carboxyl radical, a ($C_1$-$C_6$)alkyl radical substituted with a carboxyl radical, a thio radical, a thio($C_1$-$C_6$)alkyl radical, a sulfonate radical, a ($C_1$-$C_6$)alkyl radical substituted with a sulfonate radical, a ($C_1$-$C_6$)alkylcarbonyl ($C_1$-$C_6$)alkyl radical, a di(halo($C_3$-$C_6$)alkyl)amino radical, an acetamido radical, an aryloxy radical, an aryloxy($C_1$-$C_6$) alkyl radical, an ethenyl radical, an ethenylcarbonyl radical, a group $NR_6R_7$, $R_6$ and $R_7$ possibly forming, together with the nitrogen atom to which they are attached, a non-aromatic $C_5$, $C_6$ or $C_7$ ring, optionally interrupted with one or more heteroatoms such as a nitrogen, oxygen or sulfur atom, an alkylene chain possibly containing an oxygen or sulfur atom and possibly ending with a cyano, $C_1$-$C_6$ alkylsulfonyl or $C_1$-$C_6$ alkylcarbonyl group; two adjacent groups of B possibly forming an aromatic or heteroaromatic ring, which is unsubstituted or substituted with one or more substituents chosen from halo, hydroxyl, alkyl, haloalkyl, alkoxy, amino, mono- or dialkylamino, mono- or dihydroxyalkylamino and carboxyl radicals, or a ring of —O—C$_r$H$_{2r}$—O— type in which r represents an integer equal to 1 or 2. Preferably, B is unsubstituted or substituted with one or more groups chosen from a hydroxyl radical; an amino radical; a di(($C_1$-$C_6$)alkyl)amino radical; a $C_1$-$C_6$ alkyl radical; an acetamido radical; a pyridinium group; a tri($C_1$-$C_6$)alkylammonium group. By way of example, B may be substituted with a hydroxyl radical; an amino radical; a dimethylamino radical; an ethyl radical; an acetamido radical; a pyridinium group; a trimethylammonium group.

The cationic groups of the quaternary ammonium type may be chosen, for example, from trialkylammonium, oxazolium, thiazolium, imidazolium, pyrazolium, pyridinium, pyrrolium, triazolium, isoxazolium, isothiazolium, pyrimidinium, pyrazinium, triazinium, pyridazinium, indolium, quinolinium and isoquinolinium groups, which may be substituted or unsubstituted, and may be linked to the nucleus A or to the nucleus B via any of their unsubstituted carbon atoms.

Examples that may be mentioned of compounds of formula (I) for which Y is an oxygen atom include 9a-[2-[4-(dimethylamino)phenyl]-1,3-butadienyl]-2,3,9,9a-tetrahydro-9,9-dimethyloxazolo[3,2-a]indole-7-carboxylic acid; [9a-[2-[4-(dimethylamino)phenyl]-ethenyl]-2,3,9,9a-tetrahydro-9,9-dimethyloxazolo[3,2-a]indol-7-yl]phosphonic acid; 4-[2-(9,9-diethyl-2,3-dihydro-7-methoxyoxazolo[3,2-a]indol-9a(9H)-yl)ethenyl]-N,N-diethylbenzenamine; [3-[9a-[2-[4-(dimethylamino)phenyl]ethenyl]-2,3,9,9a-tetrahydro-9,9-dimethyloxazolo[3,2-a]indol-7-yl]propyl]phosphonic acid; 4-[2-(2,3-dihydro-9,9-dimethyloxazolo[3,2-a]-indol-9a(9H)-yl)ethenyl]-N-methyl-N-phenylbenzenamine; 4-[2-(2,3-dihydro-9,9-dimethyloxazolo[3,2-a]indol-9a(9H)-yl)ethenyl]-3-ethoxy-N,N-diethylbenzenamine; 4-[2-(2,3-dihydro-9,9-dimethyloxazolo[3,2-a]indol-9a(9H)-yl)ethenyl]-N-ethyl-N-(2-methylpropyl)benzenamine; 4-[2-(2,3-dihydrooxazolo[3,2-a]indol-9a(9H)-yl)ethenyl]-N,N-dimethylbenzenamine; 4-[4-(2,3-dihydro-7,9,9-trimethyloxazolo[3,2-a]indol-9a(9H)-yl)-1,3-butadienyl]-N,N-dimethylbenzenamine; 4-[4-(2,3-dihydro-9,9-dimethyl-7-nitrooxazolo[3,2-a]indol-9a(9H)-yl)-1,3-butadienyl]-N,N-dimethylbenzenamine; 9a-[4-[4-(dimethylamino)phenyl]-1,3-butadienyl]-2,3,9,9a-tetra-hydro-9,9-dimethyloxazolo[3,2-a]indole-7-carbonitrile; 9a-[2-[4-(dimethylamino)phenyl]ethenyl]-2,3,9,9a-tetra-hydro-9,9-dimethyloxazolo[3,2-a]indole-7-carbonitrile; 4-[2-(2,3-dihydro-9,9-dimethyloxazolo[3,2-a]indol-9a(9H)-yl)ethenyl]-N,N-dimethylbenzenamine; 9a-[2-[4-(dimethylamino)phenyl]ethenyl]-2,3,9,9a-tetrahydro-9,9-dimethyloxazolo[3,2-a]indole-7-sulfonic acid methyl ester; N,N-bis(2-chloroethyl)-4-[2-(2,3-dihydro-9,9-dimethyloxazolo[3,2-a]indol-9a(9H)-yl)ethenyl]benzenamine; 9a-[2-[4-(dimethylamino)phenyl]ethenyl]-9,9a-dihydro-9,9-dimethyl-7-(octylsulfonyl)oxazolo[3,2-a]-indol-2(3H)-one; 9a-[2-[4-(dimethylamino)phenyl]-ethenyl]-9,9a-dihydro-9,9-dimethyl-7-(phenylsulfonyl)-oxazolo[3,2-a]indol-2(3H)-one; 9a-[2-[4-(dimethylamino)phenyl]-1-methylethenyl]-9,9a-dihydro-9,9-dimethyl-7-(methylsulfonyl)oxazolo[3,2-a]indol-2(3H)-one; 9a-[2-[4-(dimethylamino)phenyl]ethenyl]-9,9a-dihydro-9,9-dimethyl-7-(methylsulfonyl)oxazolo[3,2-a]indol-2(3H)-one; 4-[2-[2,3-dihydro-9,9-dimethyl-7-(methylsulfonyl)oxazolo[3,2-a]indol-9a(9H)-yl]ethenyl]-N,N-dimethylbenzenamine; 4-[2-[9-(ethoxymethyl)-2,3-dihydro-9-methyl-7-(methylsulfonyl)oxazolo[3,2-a]indol-9a(9H)-yl]ethenyl]-N,N-dimethylbenzenamine; 4-[2-[2,3-dihydro-2,9,9-trimethyl-7-(methylsulfonyl)oxazolo-[3,2-a]indol-9a(9H)-yl]ethenyl]-N,N-dimethylbenzenamine; 4-[2-[2,3-dihydro-9,9-dimethyl-7-(methylsulfonyl)oxazolo[3,2-a]indol-9a(9H)-yl]-1-propenyl]-N,N-dimethylbenzenamine; N,N-dibutyl-4-[2-[2,3-dihydro-9,9-dimethyl-7-(methylsulfonyl)oxazolo[3,2-a]indol-9a(9H)-yl]ethenyl]benzenamine; 4-[2-[2,3-dihydro-9,9-dimethyl-7-(phenylsulfonyl)oxazolo[3,2-a]indol-9a(9H)-yl]ethenyl]-N,N-dimethyl; 4-[2-[2,3-dihydro-9,9-dimethyl-7-(octylsulfonyl)oxazolo[3,2-a]indol-9a(9H)-yl]ethenyl]-N,N-dimethylbenzenamine; N-[4-[2-[7-(butylsulfonyl)-2,3-dihydro-9,9-dimethyloxazolo[3,2-a]indol-9a(9H)-yl]ethenyl]phenyl]acetamide; 4-[2-[7-(butylsulfonyl)-2,3-dihydro-9,9-dimethyloxazolo[3,2-a]indol-9a(9H)-yl]ethenyl]-N,N-dimethylbenzenamine; 4-[4-[2,3-dihydro-9,9-dimethyl-7-(methylsulfonyl)oxazolo[3,2-a]-indol-9a(9H)-yl]-1,3-butadienyl]-N,N-dimethylbenzenamine; 9a-[2-[4-(dimethylamino)phenyl]ethenyl]-2,3,9,9a-tetrahydro-9-methyloxazolo[3,2-a]indole-9-ethanol; 4-[2-(9,9-diethyl-2,3-dihydrooxazolo[3,2-a]-indol-9a(9H)-yl)ethenyl]-N,N-dimethylbenzenamine; 4-[2-[2,3-dihydro-9-methyl-9-(2-phenoxyethyl)oxazolo[3,2-a]-indol-9a(9H)-yl]ethenyl]-N,N-dimethylbenzenamine; 4-[2-[9-(ethoxymethyl)-2,3-dihydro-9-methyloxazolo[3,2-a]-indol-9a(9H)-yl]ethenyl]-N,N-dimethylbenzenamine; 4-[2-(11,11-dimethylbenz[e]oxazolo[3,2-a]indol-10a(11H)-yl)-ethenyl]-N,N-dimethylbenzenamine; 4-[2-(7-methoxy-9,9-dimethyloxazolo[3,2-a]indol-9a(9H)-yl)ethenyl]-N,N-dimethylbenzenamine; 4-[2-(9,9-dimethyloxazolo[3,2-a]-indol-9a(9H)-yl)ethenyl]-N,N-dimethylbenzenamine; 9a-[2-[4-(dimethylamino)phenyl]ethenyl]-3-ethyl-9,9a-dihydro-9,9-dimethyloxazolo[3,2-a]indol-2(3H)-one; 7-chloro-9a-[2-[4-(dimethylamino)phenyl]ethenyl]-9,9a-dihydro-3,9,9-trimethyloxazolo[3,2-a]indol-2(3H)-one; 9a-[2-[4-(dibutylamino)phenyl]ethenyl]-9,9a-dihydro-9,9-dimethyloxazolo[3,2-a]indol-2(3H)-one; 9a-[2-[4-(dimethylamino)phenyl]ethenyl]-9,9a-dihydro-9-(2-hydroxyethyl)-9-methyloxazolo[3,2-a]indol-2(3H)-one; 9a-[2-[4-(dimethylamino)phenyl]-1-propenyl]-9,9a-dihydro-9,9-dimethyloxazolo[3,2-a]indol-2(3H)-one; 9,9a-dihydro-7,9,9-trimethyl-9a-[2-(4-nitrophenyl)-ethenyl]oxazolo[3,2-a]indol-2(3H)-one; N-[4-[2-(2,3-dihydro-9,9-dimethyl-2-oxooxazolo[3,2-a]indol-9a(9H)-yl)ethenyl]phenyl]acetamide; 9a-[2-[4-(dimethylamino)-phenyl]ethenyl]-9,9a-dihydro-6-methoxy-9,9-dimethyl-oxazolo[3,2-a]indol-2(3H)-one; 9a-[2-[4-(dimethyl-amino)phenyl]ethenyl]-2,3,9,9a-tetrahydro-9,9-dimethyl-2-oxooxazolo[3,2-a]indole-7-carboxylic acid ethyl ester; 9a-[2-[4-(dimethylamino)phenyl]ethenyl]-9,9a-dihydro-7,9,9-trimethyloxazolo[3,2-a]indol-2(3H)-one; 10a-[2-[4-(dimethylamino)phenyl]ethenyl]-10a,11-dihydro-11,11-dimethylbenz[e]oxazolo[3,2-a]indol-9(8H)-one; 9,9a-dihydro-9,9-dimethyl-9a-[2-(4-nitrophenyl)-ethenyl]oxazolo[3,2-a]indol-2(3H)-one; 7-chloro-9a-[2-[4-(dimethylamino)phenyl]ethenyl]-9,9a-dihydro-9,9-dimethyloxazolo[3,2-a]indol-2(3H)-one; 9a-[2-[4-(dimethylamino)phenyl]ethenyl]-9,9a-dihydro-9,9-dimethyloxazolo[3,2-a]indol-2(3H)-one; 4-[2-(7-chloro-2,3-dihydro-9,9-dimethyloxazolo[3,2-a]indol-9a(9H)-yl)ethenyl]-N,N-dimethylbenzenamine; 4-[2-(2,3-dihydro-9,9-dimethyloxazolo[3,2-a]indol-9a(9H)-yl)ethenyl]-N,N-dimethylbenzenamine; 4-[2-(7-chloro-2,3-dihydro-2,9,9-trimethyloxazolo[3,2-a]indol-9a(9H)-yl)ethenyl]-N,N-dimethylbenzenamine; 4-[2-(2,3-dihydro-9,9-dimethyloxazolo[3,2-a]indol-9a(9H)-yl)-1-methylethenyl]-N,N-dimethylbenzenamine; 4-[2-(2,3-dihydro-9,9-dimethyloxazolo[3,2-a]indol-9a(9H)-yl)ethenyl]-N,N-diethylbenzenamine; 2,3,9,9a-tetrahydro-7-methoxy-9,9-dimethyl-9a-[2-(4-nitrophenyl)ethenyl]oxazolo[3,2-a]-indole; 4-[2-(2,3-dihydro-9,9-dimethyl-7-nitrooxazolo-[3,2- a]indol-9a(9H)-yl)ethenyl]-N,N-dimethylbenzenamine; N,N-dibutyl-4-[2-(2,3-dihydro-9,9-dimethyloxazolo[3,2-a] indol-9a(9H)-yl)ethenyl]benzenamine; 2,3,9,9a-tetrahydro-9,9-dimethyl-7-nitro-9a-[2-(4-nitrophenyl)ethenyl]oxazolo [3,2-a]indole; 7-chloro-2,3,9,9a-tetrahydro-9,9-dimethyl-9a-[2-(4-nitrophenyl)-ethenyl]oxazolo[3,2-a]indole; 4-[2-(2,3-dihydro-7-iodo-9,9-dimethyloxazolo[3,2-a]indol-9a(9H)-yl)ethenyl]-N,N-dimethylbenzenamine; 4-[2-(2,3-dihydro-5-methoxy-9,9-dimethyloxazolo[3,2-a]indol-9a(9H)-yl) ethenyl]-N,N-dimethylbenzenamine; 4-[2-(2,3-dihydro-7-methoxy-9,9-dimethyloxazolo[3,2-a]indol-9a(9H)-yl) ethenyl]-N,N-dimethylbenzenamine; 4-[4-(2,3-dihydro-9,9-dimethyloxazolo[3,2-a]indol-9a(9H)-yl)-1,3-butadienyl]-N,N-diethylbenzenamine; 4-[4-(7-chloro-2,3-dihydro-9,9-dimethyloxazolo[3,2-a]indol-9a(9H)-yl)-1,3-butadienyl]-N,N-dimethylbenzenamine; 4-[4-(2,3-dihydro-9,9-dimethyloxazolo[3,2-a]indol-9a(9H)-yl)-1,3-butadienyl]-N,N-dimethylbenzenamine; 4-[4-(2,3-dihydro-7-methoxy-9,9-dimethyloxazolo[3,2-a]indol-9a(9H)-yl)-1,3-butadienyl]-N,N-dimethylbenzenamine; 2,3,9,9a-tetrahydro-7,9,9-trimethyl-9a-[2-(4-nitrophenyl)ethenyl]oxazolo-[3,2-a] indole; N-[4-[2-(2,3-dihydro-9,9-dimethyloxazolo[3,2-a] indol-9a(9H)-yl)ethenyl]phenyl]acetamide; 4-[2-(2,3-dihydro-6-methoxy-9,9-dimethyloxazolo[3,2-a]-indol-9a (9H)-yl)ethenyl]-N,N-dimethylbenzenamine; 4-[2-(8,9-dihydro-11,11-dimethylbenz[e]oxazolo[3,2-a]indol-10a (11H)-yl)ethenyl]-N,N-dimethylbenzenamine; 4-[2-(2,3-dihydro-7,9,9-trimethyloxazolo[3,2-a]indol-9a(9H)-yl) ethenyl]-N,N-dimethylbenzenamine; 2,3,9,9a-tetrahydro-9,9-dimethyl-9a-[2-(4-nitrophenyl)ethenyl]-oxazolo[3,2-a] indole; 9,9a-dihydro-9,9-dimethyl-9a-[2-(9-methyl-9H-carbazol-3-yl)ethenyl]-7-(methylsulfonyl)-oxazolo[3,2-a] indol-2(3H)-one; 9a-[2-(9-hexyl-9H-carbazol-3-yl)ethenyl]-2,3,9,9a-tetrahydro-9,9-dimethyl-7-(phenylsulfonyl) oxazolo[3,2-a]indole; 2,3,9,9a-tetrahydro-9,9-dimethyl-7-(methylsulfonyl)-9a-[2-(9-octyl-9H-carbazol-3-yl)ethenyl] oxazolo[3,2-a]-indole; 9a-[2-(9-butyl-6-methoxy-9H-carbazol-3-yl)-ethenyl]-2,3,9,9a-tetrahydro-9,9-dimethyloxazolo[3,2-a]indole-7-carboxylic acid ethyl ester; 9a-[2-(9-ethyl-9H-carbazol-3-yl)ethenyl]-2,3,9,9a-tetrahydro-9,9-dimethyloxazolo[3,2-a]indole-7-sulfonic acid methyl ester; 3-chloro-6-[2-[2,3-dihydro-9,9-dimethyl-7-(methylsulfonyl)oxazolo[3,2-a]indol-9a(9H)-yl]ethenyl]-9-octyl-9H-carbazole; 3-[2-[2,3-dihydro-9,9-dimethyl-7-(methylsulfonyl)oxazolo[3,2-a]indol-9a(9H)-yl]ethenyl]-9-methyl-9H-carbazole; 3-[2-[9-(2-ethoxyethyl)-2,3-dihydro-9-methyl-7-(methylsulfonyl)oxazolo[3,2-a]indol-9a(9H)-yl] ethenyl]-9H-carbazole; 9a-[2-(9-hexyl-9H-carbazol-3-yl) ethenyl]-2,3,9,9a-tetrahydro-9-(2-hydroxyethyl)-9-methyloxazolo[3,2-a]indole-7-carboxylic acid ethyl ester; 2,3,9,9a-tetrahydro-9,9-dimethyl-9a-[2-(9-octyl-9H-carbazol-3-yl)ethenyl]oxazolo[3,2-a]-indole-7-carboxylic acid ethyl ester; 9a-[2-(9-butyl-9H-carbazol-3-yl)ethenyl]-2,3,9,9a-tetrahydro-9,9-dimethyloxazolo[3,2-a]indole-7-carboxylic acid ethyl ester; 2,3,9,9a-tetrahydro-9,9-dimethyl-9a-[2-(9-methyl-9H-carbazol-3-yl)ethenyl]oxazolo[3,2-a]indole-7-carboxylic acid ethyl ester; 9a-[2-(9-butyl-6-ethoxy-9H-carbazol-3-yl)ethenyl]-2,3,9,9a-tetrahydro-N,N,9,9-tetramethyloxazolo[3,2-a]indol-7-amine; 2,3,9,9a-tetrahydro-9-methyl-9a-[2-(9-methyl-9H-carbazol-3-yl)-ethenyl]oxazolo[3,2-a]indole-9-ethanol; 9a-[2-(9-butyl-9H-carbazol-3-yl)ethenyl]-2,3,9,9a-tetrahydro-N,N,9,9-tetramethyloxazolo[3,2-a]indol-7-amine; 3-[2-(2,3-dihydro-6-methoxy-9,9-dimethyloxazolo[3,2-a]indol-9a(9H)-yl) ethenyl]-9-methyl-9H-carbazole; 3-[2-(2,3-dihydro-9,9-dimethyloxazolo[3,2-a]indol-9a(9H)-yl)-1-propenyl]-9-methyl-9H-carbazole; 3-[2-(7-chloro-2,3-dihydro-9,9-dimethyloxazolo[3,2-a]indol-9a(9H)-yl)-ethenyl]-9-methyl-9H-carbazole; 3-bromo-6-[2-(2,3-dihydro-9,9-dimethyloxazolo[3,2-a]indol-9a(9H)-yl]-ethenyl]-9-ethyl-9H-carbazole; 3-[2-(2,3-dihydro-9,9-dimethyloxazolo[3,2-a]indol-9a(9H)-yl)ethenyl]-9-methyl-9H-carbazole.

Preferably, the compound(s) of formula (I) for which Y represents an oxygen atom is (are) chosen from the compounds given in the table below:

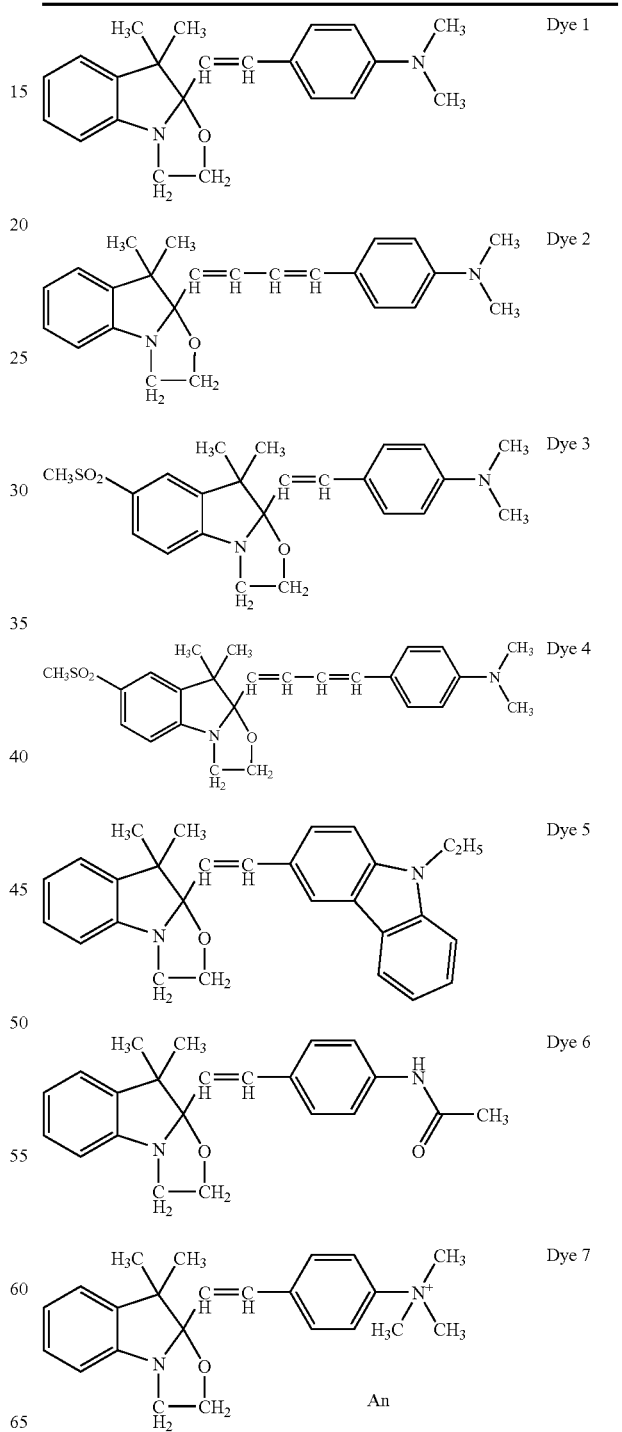

-continued

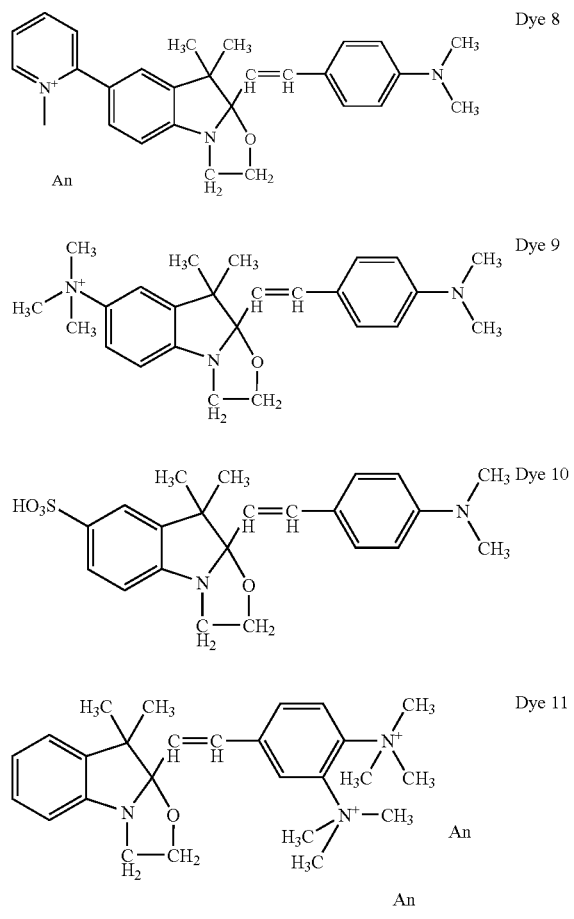

In the above table, An represents a counterion as defined above.

Preferably, the compounds are chosen from dyes 1 to 6 and 8 above.

As examples of compounds of formula (I) for which Y is a sulfur atom, mention may be made of 3,3-dimethyl-2-(p-dimethylaminostyryl)indolino[1,2-b]-thiazoline; 3,3,5-trimethyl-2-(p-dimethylaminostyryl)-indolino[1,2-b]thiazoline; 3,3,5-trimethyl-2-(p-chlorostyryl)indolino[1,2-b]thiazoline; 3,3,5-trimethyl-2-[2-(thienyl)vinyl]indolino[1,2-b]thiazoline; 3,3-dimethyl-5-methoxy-2-[22-(9-ethylcarbazolyl)vinyl]indolino[1,2-b]thiazoline; 3,3-dimethyl-5-carboethoxy-2-(p-dimethylaminostyryl)indolino[1,2-b]thiazoline; 3,3-dimethyl-5-chloro-2-[2-(benzothiazolyl)vinyl]indolino[1,2-b]-thiazoline; 3,3-dimethyl-5-methoxy-2-(p-dimethylaminostyryl)indolino[1,2-b]thiazoline; 3,3-dimethyl-5-carboethoxy-2-(3,4-methylenedioxystyryl) indolino[1,2-b]-thiazoline; 3,3-dimethyl-5-chloro-2-(p-methylstyryl)-indolino[1,2-b]thiazoline; 3,3-dimethyl-5-chloro-2-(p-methoxystyryl]indolino[1,2-b]thiazoline; 3,3,5-trimethyl-2-(p-acetylaminostyryl)indolino[1,2-b]-thiazoline; 3,3-dimethyl-5-methoxy-2-(3-hydroxy-4-methoxystyryl)indolino[1,2-b]thiazoline; 3,3-dimethyl-5-carboethoxy-2-(o-cyanostyryl)indolino[1,2-b]thiazoline; 3,3-dimethyl-5-chloro-2-(p-dimethylaminostyryl)-indolino [1,2-b]thiazoline; 3,3-dimethyl-5-methylsulfonyl-2-(p-dimethylaminostyryl)indolino[1,2-b]thiazoline; 3,3-dimethyl-5-phenylsulfonyl-2-(p-dimethylaminostyryl)indolino[1,2-b] thiazoline; 3,3-dimethyl-5-ethoxycarboxy-2-(p-dimethylaminostyryl)indolino[1,2-b]-thiazoline.

The compounds of formula (I) present in the composition of the present invention may be prepared, for example, according to the preparation modes as described in patents FR 2 285 439 and U.S. Pat. No. 4,380,629. These preparation modes may be adapted to the cationic compounds of formula (I) by adding a quaternization step.

By way of example of synthesis of a compound of formula (I) with Y representing an oxygen atom, the synthesis of dye 8 may be performed according to the following reaction scheme:

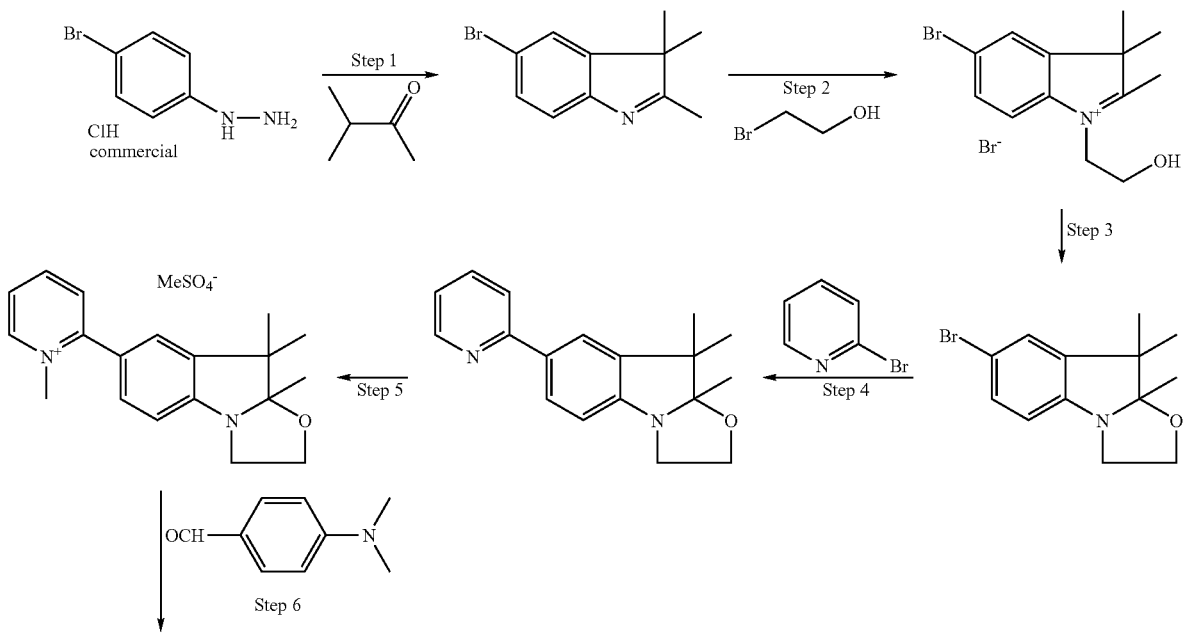

-continued

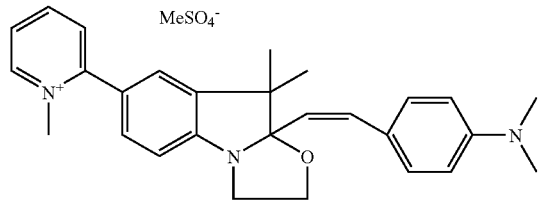

As an example of synthesis of a compound of formula (I) with Y representing a sulfur atom, it is possible to perform the synthesis as follows:

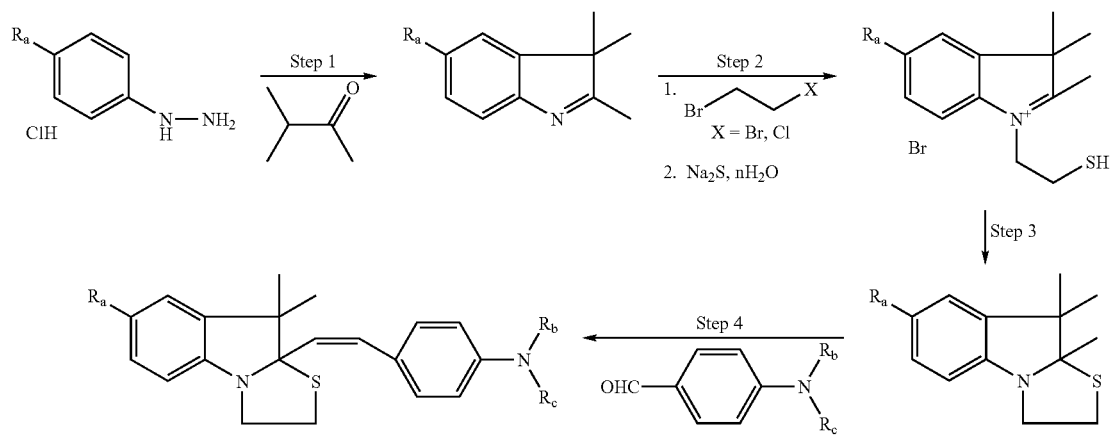

The compound(s) chosen from the compounds of formula (I), and the addition salts thereof, generally represent(s) from 0.0001% to 30% by weight relative to the total weight of the composition, more particularly from 0.001% to 10% by weight relative to the total weight of the composition and preferably from 0.01% to 5% by weight relative to the total weight of the composition.

In general, the addition salts of the compounds of formula (I) that may be used in the context of the invention are especially chosen from the acid-addition salts such as the hydrochlorides, hydrobromides, sulfates, methosulfates, gluconates, citrates, succinates, tartrates, lactates, tosylates, benzenesulfonates, phosphates and acetates, and the salts of addition with a base such as sodium hydroxide, potassium hydroxide, ammonia and amines, including alkanolamines.

As indicated above, the composition according to the invention comprises at least one thiol compound other than the compounds of formula (I), comprising at least one thiol function (SH) and a saturated or unsaturated group containing from 1 to 20 carbon atoms, said group being optionally interrupted with one or more nonadjacent groups (separated by at least one carbon atom) chosen from —O—, —S—, —S—S—, amino (—NR—), carbonyl (—CO—), oxycarbonyl (—O—CO—), aminocarbonyl (—NR—CO—), aromatic or heteroaromatic, nucleus, the amino groups being unsubstituted or substituted with one or two $C_1$-$C_6$ alkyl radicals; on condition that the sulfur atom of the thiol function is attached to said group via a carbon atom.

Moreover, the group containing from 1 to 20 carbon atoms may be optionally substituted with one or more hydroxyl, $C_1$-$C_6$ alkoxy, hydroxycarbonyl, ($C_1$-$C_6$)alkoxycarbonyl, amino, aminocarbonyl or alkylcarbonylamino, in which the amino function is unsubstituted or substituted with one or two $C_1$-$C_6$ alkyl radicals.

Preferably, the thiol compound comprises one or two thiol functions (SH), preferably a thiol function, and a saturated group containing from 2 to 10 carbon atoms, said group being optionally interrupted with a group chosen from carbonyl (—CO—) and oxycarbonyl (—O—CO—) groups; on condition that the sulfur atom of the thiol group is attached to said group via a carbon atom.

Moreover, the group may be optionally substituted with one or more hydroxyl, ($C_1$-$C_6$)alkoxycarbonyl, or amino that is unsubstituted or substituted with one or two $C_1$-$C_6$ alkyl radicals.

In accordance with one particular embodiment of the invention, the thiol compound is chosen from thioglycolic acid, thiolactic acid, mercaptopropionic acid, cysteamine, thienosuccinic acid, cysteine, acetylcysteine, glyceryl thioglycolate, thioglycerol, alkali metal (sodium or potassium), alkaline-earth metal (calcium) or ammonium salts thereof, and also mixtures thereof.

Usually, the content of thiol compound is between 0.001% and 30% by weight relative to the total weight of the composition, more particularly between 0.01% and 15% by weight relative to the total weight of the composition, preferably between 0.1% and 10% by weight relative to the total weight of the composition and even more preferably between 0.5% and 5% by weight relative to the total weight of the composition.

It should be noted that the thiol compound may be mixed with the composition comprising the compound(s) of formula (I) and thus stored. According to another possibility, the thiol compound is mixed with the composition comprising the compound(s) of formula (I) only at the time of use of said composition.

The composition according to the invention may also comprise one or more additional direct dyes, which may be chosen especially from nitrobenzene dyes, azo direct dyes, methine direct dyes and natural dyes. These direct dyes may be of nonionic, anionic or cationic nature.

When they are present, the content of additional direct dye(s) generally represents from 0.001% to 20% by weight relative to the total weight of the composition and preferably from 0.01% to 10% by weight relative to the total weight of the composition.

The composition according to the invention may also comprise one or more oxidation dyes chosen from the oxidation bases and couplers conventionally used in oxidation dyeing.

The oxidation bases may be chosen from para-phenylenediamines, bis(phenyl)alkylenediamines, para-aminophenols, bis-para-aminophenols, ortho-aminophenols, ortho-phenylenediamines and heterocyclic bases, and the addition salts thereof.

The couplers may be chosen from meta-phenylenediamines, meta-aminophenols, meta-diphenols, naphthalene-based couplers and heterocyclic couplers, and the addition salts thereof.

When they are present, the content of oxidation dye(s) generally represents from 0.001% to 20% by weight relative to the total weight of the composition and preferably from 0.01% to 10% by weight relative to the total weight of the composition.

In accordance with one preferred embodiment of the invention, the composition does not comprise any additional direct dye or any oxidation dye.

The composition may also comprise one or more acidifying agents and/or one or more basifying agents usually used in the dyeing of keratin fibers.

Among the acidifying agents that may be mentioned, for example, are mineral acids, for instance hydrochloric acid, nitric acid or sulfuric acid, or organic acids, for instance compounds comprising at least one carboxylic, acid function, such as acetic acid, tartaric acid, citric acid, lactic acid, succinic acid or malic acid, a sulfonic acid function, a phosphonic acid function or a phosphoric acid function.

Among the basifying agents that may be mentioned, for example, are:

basic amino acids;

alkali metal or alkaline-earth metal carbonates or bicarbonates;

silicates or metasilicates;

the compounds of formula (III) below:

$$X(OH)_n \quad (III)$$

in which:

X represents a potassium, lithium, sodium or ammonium ion $N^+R_8R_9R_{10}R_{11}$ with $R_5$, $R_9$, $R_{10}$ and $R_{11}$, which may be identical or different, denoting a $C_2$-$C_4$ alkyl radical when n is equal to 1;

X represents a magnesium or calcium atom when n is equal to 2;

and in particular sodium or potassium hydroxide;

the compounds of formula (IV) below:

$$R_{12}\diagdown N\diagup R_{13} \atop | \atop R_{14} \quad (IV)$$

in which:

$R_{12}$ represents a hydrogen atom; a $C_1$-$C_6$ alkyl radical; a $C_1$-$C_6$ monohydroxyalkyl radical; a $C_2$-$C_6$ polyhydroxyalkyl radical;

$R_{13}$ and $R_{14}$, which may be identical or different, represent a hydrogen atom; a $C_1$-$C_6$ alkyl radical; a $C_1$-$C_6$ monohydroxyalkyl radical; a $C_2$-$C_6$ polyhydroxyalkyl radical;

and in particular ammonia and alkanolamines such as monoethanolamine, diethanolamine and triethanolamine, and derivatives thereof;

the compounds of formula (V) below:

$$\begin{array}{c} R_{15}\diagdown \phantom{N-W-N} \diagup R_{16} \\ N-W-N \\ \diagup \phantom{N-W-N} \diagdown \\ R_{17} \phantom{N-W-N} R_{18} \end{array} \quad (V)$$

in which:

W is a propylene residue optionally substituted with a hydroxyl group or a $C_1$-$C_4$ alkyl radical;

$R_{15}$, $R_{16}$, $R_{17}$ and $R_{18}$, which may be identical or different, represent a hydrogen atom or a $C_1$-$C_4$ alkyl or $C_1$-$C_4$ hydroxyalkyl radical.

For the purposes of the present invention, the term "basic amino acid" means either (i) an amino acid containing, in addition to the amine function located a to the carboxyl group, an additional cationic (or basic) group; or (II) an amino acid containing a cationic (or basic) side chain (hydrophilic); or (III) an amino acid bearing a side chain consisting of a nitrogenous base. These definitions are generally known and published in general biochemistry texts such as J. H. Weil (1983) pages 5 et, seq., Lubert Stryer (1995) page 22, A. Lehninger (1993) pages 115-116 and de Boeck-Wesmael (1994) pages 57-59.

The basic amino acids in accordance with the invention are preferably chosen from those corresponding to formula (D) below:

$$R_{19}-CH_2-CH\diagup {NH_2} \diagdown {CO_2H} \quad (D)$$

in which $R_{19}$ denotes a group chosen from:

$$\begin{array}{c}\diagup NH \\ \langle\phantom{N}\rangle \\ N\end{array} \quad ; \quad -(CH_2)_3NH_2; \quad -(CH_2)_2NH_2;$$

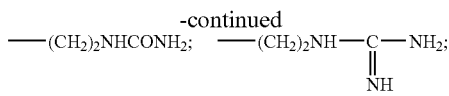

Among the compounds of formula (D) that may be mentioned, for example, are histidine, lysine, ornithine, citrulline and arginine.

The suitable dyeing medium, also known as the dye support, generally consists of water or of at least one organic solvent, or of a mixture of water and of at least one organic solvent. Examples of organic solvents that may be mentioned include ketones such as acetone; linear or branched monoalcohols or diols, which are preferably saturated, containing 2 to 10 carbon atoms, such as ethyl alcohol, isopropyl alcohol, hexylene glycol (2-methyl-2,4-pentanediol), neopentyl glycol and 3-methyl-1,5-pentanediol; aromatic alcohols such as benzyl alcohol and phenylethyl alcohol; polyols or polyol ethers, for instance ethylene glycol monomethyl, monoethyl and monobutyl ether, 2-butoxyethanol, propylene glycol or ethers thereof, for instance propylene glycol monomethyl ether, butylene glycol or dipropylene glycol; and also diethylene glycol alkyl ethers, especially of $C_1$-$C_4$, for instance diethylene glycol monoethyl ether or monobutyl ether, alone or as a mixture.

The solvents are generally present in proportions of between 1% and 40% by weight relative to the total weight of the composition; and preferably between 5% and 30% by weight relative to the total weight of the composition.

The composition according to the invention may also contain various adjuvants conventionally used in hair compositions, such as anionic, cationic, nonionic, amphoteric or zwitterionic surfactants or mixtures thereof, anionic, cationic, nonionic, amphoteric or zwitterionic polymers or mixtures thereof, mineral or organic thickeners, and in particular anionic, cationic, nonionic and amphoteric associative polymeric thickeners, antioxidants, penetrants, sequestrants, fragrances, buffers, dispersants, conditioning agents, for instance cationic or amphoteric polymers, cations, volatile or nonvolatile, modified or non-modified silicones, chitosans or chitosan derivatives, film-forming agents, ceramides, preserving agents and opacifiers.

The above adjuvants are generally present in an amount for each of between 0.01% and 20% by weight relative to the weight of the composition.

Needless to say, a person skilled in the art will take care to select this or these optional additional compounds such that the advantageous properties intrinsically associated with the composition that is useful in the context of the invention are not, or are not substantially, adversely affected by the envisaged addition(s).

According to one variant of the invention, the pH of the composition is greater than the pKa of the compound of formula (I) and less than or equal to 12. Advantageously, the pH is between 8 and 12. In the context of this variant, the compound is in a substantially colorless form.

The composition according to the invention may be in various forms, such as in the form of liquids, creams or gels, or in any other form that is suitable for dyeing keratin fibers, and especially human hair.

The process for dyeing keratin fibers in accordance with the invention is a process in which the composition that has just been described is applied to wet or dry keratin fibers, for a sufficient period of time, this application being followed, where appropriate, by rinsing.

As the compounds of formula (I) are colorless, the color imparted by the compounds of formula (I) is therefore revealed subsequently. This is done by using revealing agents such as light, an electrical current, heat, an acidifying agent, a solvent, an electromagnetic radiation.

When the coloration is revealed by the action of heat, the keratin fibers may be heated using a hood, a hairdryer, a crimping iron or a smoothing iron.

As regards the nature of the acidifying agents and solvents, reference may be made to the account given previously in the description.

Advantageously, when the revealing agent is an acidifying agent, it is preferred to use at least one organic acid, for instance compounds comprising at least one carboxylic acid function such as acetic acid, tartaric acid, citric acid, lactic acid, succinic acid or malic acid.

According to a first variant of the invention, a post-treatment is carried out by the action of a revealing agent such as light, an electrical current, heat, an acidifying agent and/or a solvent or an electromagnetic radiation, or of a combination of several of these revealing agents.

According to a second variant of the invention, a pre-treatment is carried out by the action of a revealing agent such as the acidifying agents and the solvents or the combination of one or more of these revealing agents.

The interval between a pretreatment step and the application of the composition according to the invention, or alternatively between the application of the composition and a post-treatment step, may be between 5 minutes and 1 hour.

It is similarly possible to reduce this interval to zero, which amounts to applying the composition according to the invention immediately after applying the composition comprising the revealing agent in the case of a pretreatment step, or alternatively to performing the post-treatment step immediately after applying the composition according to the invention in the case of a post-treatment step.

According to another particular embodiment of the invention, although not a preferred embodiment, the composition according to the invention is applied in the presence of an oxidizing agent.

According to a first possibility, the oxidizing agent and the composition comprising the compound(s) of formula (I) are applied simultaneously. In this case, simultaneous dyeing and bleaching of the keratin fibers is performed. According to this possibility, the oxidizing agent is preferably added to the composition just at the time of use.

According to a second possibility, the oxidizing agent is added once the composition comprising the compound(s) of formula (I) has (have) been applied.

The oxidizing agent may be chosen from hydrogen peroxide, urea peroxide, alkali metal bromates, persalts, peracids and enzymes of oxidase type.

The leave-on time for the composition according to the invention optionally comprising an oxidizing agent, or the application time for the revealing agent or the application time for the composition comprising an oxidizing agent, is generally between 5 minutes and 1 hour and preferably between 15 minutes and 1 hour.

The application temperature of the composition according to the invention comprising an oxidizing agent or otherwise, of the revealing agent and of the oxidizing composition is generally set between room temperature and 80° C. and preferably between room temperature and 60° C. It should be noted that when the revealing agent is heat, the application temperature is between 60 and 120° C.

A subject of the present invention is also a multicompartment device for performing the process for dyeing keratin fibers in accordance with the invention.

The multicompartment device of the invention contains in a first compartment a composition comprising at least one compound chosen from the compounds of formula (I), and the addition salts thereof, and in a second compartment at least one third compound, defined previously.

According to one particular embodiment of the invention, the multicompartment device of the invention contains in a third compartment at least one oxidizing agent as defined previously.

Finally, the invention also relates to a process for effacing the coloration obtained using the composition according to the invention.

With this aim, the dyed keratin fibers in accordance with the invention are treated with an effacing composition comprising at least one basifying agent as described previously, in a content such that the pH of the treated fibers is greater than the pKa of the compound(s) of formula (I) present in the composition giving rise to the coloration.

The effacing composition is applied to the wet or dry fibers, usually with a leave-on time of between 5 minutes and 1 hour and preferably between 5 and 30 minutes.

Conventionally, the application temperature of this composition is between room temperature and 80° C. and preferably between room temperature and 60° C.

The examples that follow serve to illustrate the invention without, however, being limiting in nature.

EXAMPLE 1

The following formulations were prepared:

|  | A Comparative | B Invention |
|---|---|---|
| Dye (*) | 0.07% | 0.07% |
| Benzyl alcohol | 8.4% | 8.4% |
| Ethanol | 25.2% | 25.2% |
| Monoethanolamine | 4.2% | 4.2% |
| Thioglycolic acid | 0% | 1% |
| Distilled water | qs 100% | qs 100% |

(*) Dye:

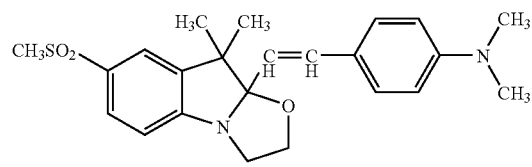

Each formulation is applied to locks of natural dry hair containing 90% white hairs, with a leave-on time of 30 minutes at room temperature.

The colour is then revealed by applying a 0.5N hydrochloric acid solution with a bath ratio of 1.

The locks are then rinsed with clean water and dried at 60° C.

The calorimetric results (CIE L*a*b* system, specular components included, angle 10°, D65) are given below in Table 1.

| Composition | L* |
|---|---|
| A comparative | 54.3 |
| B invention | 32.2 |

It is found that the intensity of the coloration obtained by using composition B according to the invention comprising 1% thioglycolic acid is significantly higher (lower value) than the strength obtained with the comparative composition not comprising this thiol compound.

EXAMPLE 2

The formulations below according to the invention were prepared:

|  | C | D | E | F | G | H |
|---|---|---|---|---|---|---|
| Dye (*) | 0.07% | 0.07% | 0.07% | 0.07% | 0.07% | 0.07% |
| Benzyl alcohol | 8.4% | 8.4% | 8.4% | 8.4% | 8.4% | 8.4% |
| Ethanol | 25.2% | 25.2% | 25.2% | 25.2% | 25.2% | 25.2% |
| Monoethanolamine | 4.2% | 4.2% | 4.2% | 4.2% | 4.2% | 4.2% |
| Thioglycolic acid | 2% | — | — | — | — | — |
| Ammonium thioglycolate 71% | — | 3.34% | — | — | — | — |
| Ammonium dithioglycolate | — | — | 9.77% | — | — | — |
| Ammonium thiolactate (70%) | — | — | — | 3.70% | — | — |
| Cysteine | — | — | — | — | 2.63% | — |
| N-Acetyl-L-cysteine | — | — | — | — | — | 3.54% |
| Distilled water | qs 100% | qs 100% | qs 100% | qs 100% | qs 100% | qs 100% |

The following comparative formulations were prepared:

| Compound | I | J | K | L |
|---|---|---|---|---|
| Dye (*) | 0.07% | 0.07% | 0.07% | 0.07% |
| Benzyl alcohol | 8.4% | 8.4% | 8.4% | 8.4% |
| Ethanol | 25.2% | 25.2% | 25.2% | 25.2% |
| Monoethanolamine | 4.2% | 4.2% | 4.2% | 4.2% |
| Sodium thiosulfate pentahydrate (Na$_2$S$_2$O$_3$·5H$_2$O) | 5.39% | — | — | — |
| Sodium sulfite (Na$_2$SO$_3$) | — | 2.74% | — | — |
| Sodium bisulfite (sodium metabisulfite sodium pyrosulfite Na$_2$S$_2$O$_5$) | — | — | 3.54% | — |
| Sodium hydrogen sulfite | — | — | — | 2.28% |
| Distilled water | qs 100% | qs 100% | qs 100% | qs 100% |

Dye (*): the dye is the same as that used in Example 1.

The percentages in the above tables are expressed on a weight basis. The contents of thiol compounds correspond to identical mole percentage contents.

The conditions of application of the compositions are the same as those described in Example 1.

The calorimetric results (CIE L*a*b* system, specular components included, angle 10°, D65) are given in Table below.

|  | L* |
|---|---|
| Undyed hair | 63.8 |
| Formulation C invention | 35.4 |
| Formulation D invention | 50.0 |
| Formulation E invention | 37.0 |
| Formulation F invention | 41.2 |
| Formulation G invention | 43.2 |
| Formulation H invention | 50.6 |
| Formulation I comparative | 59.0 |
| Formulation J comparative | 56.0 |
| Formulation K comparative | 63.5 |
| Formulation L comparative | 56.2 |

The lower the value of L*, the greater the intensity of the coloration obtained.

The above table consequently shows that the reducing agents of thiol type cause a significant improvement in the intensity of the coloration obtained between the values of the coefficients L* for the undyed hair and for the hair dyed with compositions comprising reducing agents outside the invention, in particular mineral reducing agents.

Moreover, the composition applied to the hair is colourless, which means that the process is not soiling, and nor are the hair or washing and rinsing waters.

EXAMPLE 3

The composition below was prepared:

| Dye composition | weight % |
|---|---|
| Dye (*) | 0.07% |
| Benzyl alcohol | 5% |
| Ethanol | 25.2% |
| Monoethanolamine | 2% |
| Ammonium thioglycolate (71% AM) | 3.34% |
| Hydroxyethylcellulose | 1.5% |
| Distilled water | qs 100% |

(*) Dye:

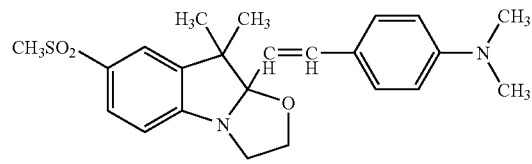

Each formulation is applied to locks of natural dry hair containing 90% white hairs, with a bath ratio of 5, for a leave-on time of 30 minutes at room temperature.

After dyeing, the hair is rinsed with clean water and then drained dry and treated with a revealing composition, the composition of which is summarized in the table below (the percentages are expressed on a weight basis):

| Revealing composition | M | N | O | P |
|---|---|---|---|---|
| Tartaric acid | 6% | — | — | — |
| Succinic acid | — | 5.9 | — | — |
| DL-Malic acid | — | — | 6.7 | — |
| Citric acid | — | — | — | 9.6 |
| NaOH qs pH | 3 | 3 | 3 | 3.2 |
| Distilled water | qs 100% | qs 100% | qs 100% | qs 100% |

Each composition is applied with a bath ratio of 1.
The locks are then rinsed with clean water and dried at 60° C.

The calorimetric results (CIE L*a*b* system, specular components included, angle 10°, D65) are given below:

|  | L* |
|---|---|
| Undyed hair | 63.8 |
| Composition M | 44.8 |
| Composition N | 39.2 |
| Composition O | 43.1 |
| Composition P | 38.9 |

The invention claimed is:

1. Composition for dyeing keratin fibres, comprising, in a suitable dyeing medium,
   a) at least one compound of formula (I), and the addition salts thereof:

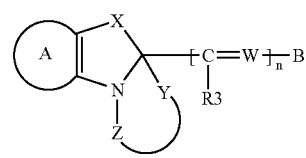

(I)

in which:

A is a substituted or unsubstituted, 5- to 16-membered, fused or non-fused aromatic or heteroaromatic nucleus;

X represents an oxygen atom, a sulphur atom or a group $CR_1R_2$;

$R_1$ and $R_2$ represent, independently of each other, a hydrogen atom, a $C_1$-$C_6$ alkyl radical, a $C_1$-$C_6$ hydroxyalkyl radical, a $C_1$-$C_6$ alkoxyalkyl radical or an alkylene chain that may contain an oxygen or sulphur atom; $R_1$ and $R_2$ may together form an aromatic or non-aromatic 5- or 6-membered ring optionally containing one or more heteroatoms such as a nitrogen, oxygen or sulphur atom;

$R_3$ represents a hydrogen atom, a halogen atom, a $C_1$-$C_6$ alkyl radical, a cyano radical, an aromatic group, a phenoxy group or a nitro radical;

W represents a group $CR_4$ or a nitrogen atom;

$R_4$ represents a hydrogen atom, a halogen atom, a $C_1$-$C_6$ alkyl radical, a cyano radical, an aromatic group, a phenoxy radical or a nitro radical;

Y represents an oxygen atom, a sulphur atom or a group $NR_5$;

$R_5$ represents a hydrogen atom or a $C_1$-$C_6$ alkyl radical;

Z represents a group —$C_pH_{2p}$—, with p being an integer between 2 and 4, which may be unsubstituted or substituted with one or more substituents chosen from halo, hydroxyl, alkyl, haloalkyl, alkoxy, amino, mono- or dialkylamino, mono- or dihydroxyalkylamino and carboxyl radicals; a group —$C_qH_{2q}CO$—, with q being an integer between 1 and 3, which may be unsubstituted or substituted with one or more substituents chosen from halo, hydroxyl, alkyl, haloalkyl, alkoxy, amino, mono- or dialkylamino, mono- or dihydroxyalkylamino and carboxyl radicals;

n represents an integer from 1 to 4;

B represents a substituted or unsubstituted, 5- to 16-membered, fused or non-fused aromatic or heteroaromatic nucleus, b) at least one thiol compound comprising at least one thiol function (SH) and a saturated or unsaturated group containing from 1 to 20 carbon atoms, said group being optionally interrupted with one or more nonadjacent groups chosen from —O—, —S—, —S—S—, amino (—NR—), carbonyl (—CO—), oxycarbonyl (—O—CO—), aminocarbonyl (—NR—CO—), aromatic or heteroaromatic nucleus, the amino groups being unsubstituted or substituted with one or two $C_1$-$C_6$ alkyl radicals; on condition that the sulphur atom of the thiol function is attached to said group via a carbon atom; said group being optionally substituted with one or more hydroxyl, $C_1$-$C_6$ alkoxy, hydroxycarbonyl, ($C_1$-$C_6$) alkoxycarbonyl, amino, aminocarbonyl or alkylcarbonylamino, in which the amino function is unsubstituted or substituted with one or two $C_1$-$C_6$ alkyl radicals.

2. The composition according to claim 1, wherein A is a benzene, anthracene, naphthalene or quinoline nucleus.

3. The composition according to claim 1, wherein A is unsubstituted or substituted with one or more groups chosen from a halo radical, a $C_1$-$C_6$ alkyl radical, a $C_1$-$C_6$ alkoxy radical, a $C_1$-$C_6$ alkylsulphonyl radical (—$SO_2$-alkyl), a $C_1$-$C_6$ alkylsulphonate radical (—$SO_3$-alkyl), a cyano radical, a trifluoromethyl radical, a $C_1$-$C_6$ alkylcarbonyl radical, a trifluoromethylsulphonyl radical (—$SO_2$-$CF_3$), a tri-fluoromethylcarbonyl radical, a phenylsulphonyl radical (—$SO_2$-Ph), a phenylsulphonate radical (—$SO_3$-Ph), a phenylcarbonyl radical, a nitro radical, a $C_1$-$C_6$ alkoxycarbonyl radical, a phosphonyl radical (—PO(OH)$_2$), a phosphonyl($C_{1-6}$)alkyl radical (—alkyl—PO(OH)$_2$), a hydroxyl radical, an amino radical, a di($C_1$-$C_6$)alkylamino radical, a (hydroxy($C_1$-$C_6$)alkyl)amino radical, a di(hydroxy($C_1$-$C_6$)alkyl)amino radical, an (amino($C_1$-$C_6$)alkyl)amino radical, a di(amino($C_1$-$C_6$)-alkyl)amino radical, a (hydroxy($C_1$-$C_6$)alkyl)(($C_1$-$C_6$)alkyl)amino radical, an (amino($C_1$-$C_6$)alkyl)(($C_1$-$C_6$)alkyl)amino radical, an (amino($C_1$-$C_6$)alkyl)-(hydroxy($C_1$-$C_6$)alkyl)amino radical, a hydroxy($C_1$-$C_6$)alkyl radical, an amino($C_1$-$C_6$)alkyl radical, a (($C_1$-$C_6$)alkyl)amino($C_1$-$C_6$)alkyl radical, a di(($C_1$-$C_6$)alkyl)-amino($C_1$-$C_6$)alkyl radical, a (hydroxy($C_1$-$C_6$)alkyl)amino($C_1$-$C_6$)alkyl radical, a di(hydroxy($C_1$-$C_6$)alkyl)amino($C_1$-$C_6$)alkyl radical, an (amino($C_1$-$C_6$)-alkyl)amino($C_1$-$C_6$)alkyl radical, a di(amino($C_1$-$C_6$)alkyl)amino($C_1$-$C_6$)alkyl radical, a (($C_1$-$C_6$)alkyl)(hydroxy($C_1$-$C_6$)alkyl)amino($C_1$-$C_6$)alkyl radical, an (amino($C_1$-$C_6$)alkyl)(($C_1$-$C_6$)alkyl)amino radical, a (hydroxy($C_1$-$C_6$)alkyl)(($C_1$-$C_6$)alkyl)-amino($C_1$-$C_6$)alkyl radical, a phenyl($C_1$-$C_6$)alkyl radical optionally substituted with one or more substituents chosen from halo, hydroxyl, alkyl, haloalkyl, alkoxy, amino, mono- or dialkylamino, mono- or dihydroxyalkylamino and carboxyl radicals, a cationic group of the quaternary ammonium type, a $C_1$-$C_6$ alkyl radical substituted with a cationic group of the quaternary ammonium type, a carboxyl radical, a ($C_1$-$C_6$)alkyl radical substituted with a carboxyl radical, a thiol radical, a thio($C_1$-$C_6$)alkyl radical, a sulphonate radical (—$SO_3$), a ($C_1$-$C_6$)alkyl radical substituted with a sulphonate radical, a ($C_1$-$C_6$)alkylcarbonyl($C_1$-$C_6$)alkyl radical, a di(halo($C_1$-$C_6$)alkyl)amino radical, an acetamido radical, an aryloxy radical, an aryloxy($C_1$-$C_6$)alkyl radical, an ethenyl radical (—CH=$CH_2$), an ethenylcarbonyl radical (—CO—CH=$CH_2$); two adjacent groups possibly forming an aromatic or heteroaromatic ring, which is unsubstituted or substituted with one or more substituents chosen from halo, hydroxyl, alkyl, haloalkyl, alkoxy, amino, mono- or dialkylamino, mono- or dihydroxyalkylamino and carboxyl radicals, or a ring of —O—$C_mH_{2m}$—O— type where m is an integer equal to 1 or 2.

4. The composition according to claim 3, wherein A is unsubstituted or substituted with one or more groups chosen from a ($C_1$-$C_6$)alkylsulphonyl radical; a pyridinium or imidazolium group, which is unsubstituted or substituted with one or more substituents chosen from halo, hydroxyl, alkyl, haloalkyl, alkoxy, amino, mono- or dialkylamino, mono- or dihydroxyalkylamino and carboxyl radicals; a tri-($C_1$-$C_6$) alkylammonium group; a sulphonate radical.

5. The composition according to claim 1, wherein X is chosen from a group $CR_1R_2$.

6. The composition according to claim 1, wherein $R_1$ and $R_2$ are chosen from a $C_1$-$C_6$ alkyl radical.

7. The composition according to claim 1, wherein $R_3$ is chosen from a hydrogen atom.

8. The composition according to claim 1, wherein W is chosen from a group $CR_4$.

9. The composition according to claim 1, wherein $R_4$ is chosen from a hydrogen atom.

10. The composition according to claim 1, wherein Y is chosen from an oxygen or sulphur atom.

11. The composition according to claim 1, wherein Z is chosen from a group —$C_pH_{2p}$—, with p being an integer between 2 and 4, which is unsubstituted or substituted with one or more substituents chosen from halo, hydroxyl, alkyl, haloalkyl, alkoxy, amino, monoalkylamino or dialkylamino, monohydroxyalkylamino or dihydroxyalkylamino and carboxyl radicals.

12. The composition according to claim 1, wherein n is equal to 1 or 2.

13. The composition according to claim 1, wherein B is a benzene, carbazole or indole nucleus.

14. The composition according to claim 1, wherein B is unsubstituted or substituted with one or more groups chosen from a halo radical, a $C_1$-$C_6$ alkyl radical, a $C_1$-$C_6$ alkoxy radical, a cyano radical, a trifluoromethyl radical, a $C_1$-$C_6$ alkylcarbonyl radical, a trifluoromethylsulphonyl radical, a trifluoromethylcarbonyl radical, a phenylsulphonyl radical, a phenylcarbonyl radical, a phenyl radical which is unsubstituted or substituted with one or more substituents chosen from halo, hydroxyl, alkyl, haloalkyl, alkoxy, amino, mono- or dialkylamino, mono- or dihydroxyalkylamino and carboxyl radicals, an acylamino radical, a hydroxyl radical, an amino radical, a di(($C_1$-$C_6$)alkyl)amino radical, a hydroxy-($C_1$-$C_6$)alkylamino radical, a di(hydroxy($C_1$-$C_6$)alkyl)amino radical, an (amino($C_1$-$C_6$)alkyl)amino radical, a di(amino ($C_1$-$C_6$)alkyl)amino radical, a (($C_1$-$C_6$)alkyl)-(hydroxy($C_1$-$C_6$)alkyl)amino radical, an (amino($C_1$-$C_6$)alkyl)(($C_1$-$C_6$) alkyl)amino radical, an (amino($C_1$-$C_6$)alkyl)(hydroxy($C_1$-$C_6$)alkyl)amino radical, a hydroxy-($C_1$-$C_6$)alkyl radical, an amino($C_1$-$C_6$)alkyl radical, a ($C_1$-$C_6$)alkylamino($C_1$-$C_6$) alkyl radical, a di(($C_1$-$C_6$)alkyl)amino($C_1$-$C_6$)alkyl radical, a (hydroxy($C_1$-$C_6$)-alkyl)amino($C_1$-$C_6$)alkyl radical, a di(hydroxy($C_1$-$C_6$)alkyl)amino($C_1$-$C_6$)alkyl radical, an amino($C_1$-$C_6$)alkylamino($C_1$-$C_6$)alkyl radical, a di(amino($C_1$-$C_6$)-alkyl)amino($C_1$-$C_6$)alkyl radical, a (($C_1$-$C_6$)alkyl)(hydroxy ($C_1$-$C_6$)alkyl)amino($C_1$-$C_6$)alkyl radical, a (($C_1$-$C_6$)alkyl) (amino($C_1$-$C_6$)alkyl)amino radical, a (hydroxy($C_1$-$C_6$)alkyl) (($C_1$-$C_6$)alkyl)amino($C_1$-$C_6$)alkyl radical, a phenyl($C_1$-$C_6$) alkyl radical which is unsubstituted or substituted with one or more substituents chosen from halo, hydroxyl, alkyl, haloalkyl, alkoxy, amino, mono- or dialkylamino, mono- or dihydroxyalkylamino and carboxyl radicals, a cationic group of the quaternary ammonium type, a ($C_1$-$C_6$)alkyl radical substituted with a cationic group of the quaternary ammonium type, a carboxyl radical, a ($C_1$-$C_6$)alkyl radical substituted with a carboxyl radical, a thiol radical, a thio($C_1$-$C_6$) alkyl radical, a sulphonate radical, a ($C_1$-$C_6$)alkyl radical substituted with a sulphonate radical, a ($C_1$-$C_6$)-alkylcarbonyl($C_1$-$C_6$)alkyl radical, a di(halo($C_1$-$C_6$)alkyl)amino radical, an acetamido radical, an aryloxy radical, an aryloxy($C_1$-$C_6$)alkyl radical, an ethenyl radical, an ethenylcarbonyl radical, a group $NR_6R_7$, $R_6$ and $R_7$ possibly forming, together with the nitrogen atom to which they are attached, a non-aromatic $C_5$, $C_6$ or $C_7$ ring, optionally interrupted with one or more heteroatoms such as a nitrogen, oxygen or sulphur atom, an alkylene chain possibly containing an oxygen or sulphur atom and possibly ending with a cyano, $C_1$-$C_6$ alkylsulphonyl or $C_1$-$C_6$ alkylcarbonyl group; two adjacent groups of B possibly forming an aromatic or heteroaromatic ring, which is unsubstituted or substituted with one or more substituents chosen from halo, hydroxyl, alkyl, haloalkyl, alkoxy, amino, mono- or dialkylamino, mono- or dihydroxyalkylamino and carboxyl radicals, or a ring of —O—$C_rH_{2r}$—O— type in which r represents an integer equal to 1 or 2.

15. The composition according to claim 14, wherein B is unsubstituted or substituted with one or more groups chosen from a hydroxyl radical; an amino radical; a di(($C_1$-$C_6$)alkyl) amino radical; a $C_1$-$C_6$ alkyl radical; an acetamido radical; a pyridinium group; a tri($C_1$-$C_6$)alkylammonium group.

16. The composition according to claim 1, wherein the at least one compound of formula (I) is chosen from 9a-[2-[4-(dimethylamino)phenyl]-1,3-butadienyl]-2,3,9,9a-tetrahydro-9,9-dimethyloxazolo[3,2-a]indole-7-carboxylic acid; [9a-[2-[4-(dimethylamino)phenyl]ethenyl]-2,3,9,9a-tetrahydro-9,9-dimethyl-oxazolo[3,2-a]indol-7-yl]phosphonic acid; 4-[2-(9,9-diethyl-2,3-dihydro-7-methoxyoxazolo[3,2-a]indol-9a(9H)-yl)ethenyl]-N,N-diethylbenzenamine; [3-[9a-[2-[4-(dimethylamino)phenyl]ethenyl]-2,3,9,9a-tetrahydro-9,9-dimethyloxazolo[3,2-a]indol-7-yl]propyl] phosphonic acid; 4-[2-(2,3-dihydro-9,9-dimethyloxazolo[3,2-a]indol-9a(9H)-yl)ethenyl]-N-methyl-N-phenylbenzenamine; 4-[2-(2,3-dihydro-9,9-dimethyloxazolo[3,2-a]indol-9a(9H)-yl)ethenyl]-3-ethoxy-N,N-diethylbenzenamine; 4-[2-(2,3-dihydro-9,9-dimethyloxazolo[3,2-a]indol-9a (9H)-yl)ethenyl]-N-ethyl-N-(2-methylpropyl)benzenamine; 4-[2-(2,3-dihydrooxazolo [3,2-a]indol-9a(9H)-yl)ethenyl]-N,N-dimethylbenzenamine; 4-[4-(2,3-dihydro-7,9,9-trimethyloxazolo [3,2-a]indol-9a(9H)-yl)-1,3-butadienyl]-N,N-dimethylbenzenamine; 4-[4-(2,3-dihydro-9,9-dimethyl-7-nitrooxazolo[3,2-a]indol-9a(9H)-yl)-1,3-butadienyl]-N,N-dimethylbenzenamine; 9a-[4-[4-(dimethylamino)-phenyl ]-1,3-butadienyl]-2,3,9,9a-tetrahydro-9,9-dimethyloxazolo[3,2-a]indole-7-carbonitrile; 9a-[2-[4-(dimethylamino)phenyl]ethenyl]-2,3,9,9a-tetrahydro-9,9-dimethyloxazolo[3,2-a]indole-7-carbonitrile; 4-[2-(2,3-dihydro-9,9-dimethyloxazolo[3,2-a]indol-9a(9H)-yl) ethenyl]-N,N-dimethylbenzenamine; 9a-[2-[4-(dimethylamino) phenyl]ethenyl]-2,3,9,9a-tetrahydro-9,9-dimethyloxazolo-[3,2-a]indole-7-sulphonic acid methyl ester; N,N-bis(2-chloroethyl)-4-[2-(2,3-dihydro-9,9-dimethyloxazolo [3,2-a]indol-9a(9H)-yl)ethenyl]benzenamine; 9a-[2-[4-(dimethylamino) phenyl]ethenyl]-9,9a-dihydro-9,9-dimethyl-7-(octylsulphonyl) oxazolo[3,2-a]indol-2(3H)-one; 9a-[2-[4-(dimethylamino)phenyl]-ethenyl]-9,9a-dihydro-9,9-dimethyl-7-(phenylsulphonyl)oxazolo[3,2-a]indol-2(3H)-one; 9a-[2-[4-(dimethylamino)phenyl]-1-methylethenyl]-9,9a-dihydro-9,9-dimethyl-7-(methylsulphonyl) oxazolo[3,2-a]indol-2(3H)-one; 9a-[2-[4-(dimethylamino) phenyl]ethenyl]-9,9a-dihydro-9,9-dimethyl-7-(methylsulphonyl)oxazolo[3,2-a]indol-2(3 H)-one; 4-[2-[2,3-dihydro-9,9-dimethyl-7-(methylsulphonyl)oxazolo[3,2-a]indol-9a(9 H)-yl]ethenyl]-N,N-dimethylbenzenamine; 4-[2-[9-(ethoxymethyl)-2,3-dihydro-9-methyl-7-(methylsulphonyl)oxazolo[3,2-a]indol-9a(9H)-yl] ethenyl]-N,N-dimethylbenzenamine; 4-[2-[2,3-dihydro-2,9,9-trimethyl-7-(methylsulphonyl)oxazolo[3,2-a]indol-9a (9H)-yl]ethenyl]-N,N-dimethylbenzenamine; 4-[2-[2,3-dihydro-9,9-dimethyl-7-(methylsulphonyl)oxazolo[3,2-a] indol-9a(9H)-yl]-1-propenyl]-N,N-dimethylbenzenamine; N,N-dibutyl-4-[2-[2,3-dihydro-9,9-dimethyl-7-(methylsulphonyl)oxazolo[3,2-a]indol-9a(9H)-yl]ethenyl]benzenamine; 4-[2-[2,3-dihydro-9,9-dimethyl-7-(phenylsulphonyl)oxazolo[3,2-a]indol-9a(9H)-yl]ethenyl]-N,N-dimethyl; 4-[2-[2,3-dihydro-9,9-dimethyl-7-(octylsulphonyl)oxazolo [3,2-a]indol-9a(9 H)-yl]ethenyl]-N,N-dimethylbenzenamine; N-[4-[2-[7-(butylsulphonyl)-2,3-dihydro-9,9-dimethyloxazolo[3,2-a]indol-9a(9H)-yl]ethenyl]phenyl] acetamide; 4-[2-[7-(butylsulphonyl)-2,3-dihydro-9,9-dimethyloxazolo[3,2-a]indol-9a(9H)-yl]ethenyl]-N,N-dimethylbenzenamine; 4-[4-[2,3-dihydro-9,9-dimethyl-7-(methylsulphonyl)oxazolo[3,2-a]indol-9a(9H)-yl]-1,3-butadienyl]-N,N-dimethyl-benzenamine; 9a-[2-[4-(dimethylamino)phenyl]ethenyl]-2,3,9,9a-tetrahydro-9-methyloxazolo[3,2-a]indole-9-ethanol; 4-[2-(9,9-diethyl-2,3-dihydrooxazolo[3,2-a]-indol-9a(9H)-yl)ethenyl]-N,N-dimethylbenzenamine; 4-[2-[2,3-dihydro-9-methyl-9-(2-phenoxyethyl)oxazolo[3,2-a]indol-9a(9H)-yl]ethenyl]-N,N-dimethylbenzenamine; 4-[2-[9-(ethoxymethyl)-2,3-dihydro-9-methyloxazolo[3,2-a]indol-9a(9H)-yl]ethenyl]-N,N-dimethylbenzenamine; 4-[2-(11,11-dimethylbenz[e]oxazolo [3,2-a]indol-10a(11 H)-yl)ethenyl]-N,N-dimethylbenzenamine; 4-[2-(7-methoxy-9,9-dimethyloxazolol3,2-a]indol-9a(9H)-yl)ethenyl]-N,N-dimethylbenzenamine; 4-[2-(9,9-dimethyloxazolo[3,2-a] indol-9a(9H)-yl)ethenyl]-N,N-dimethylbenzenamine; 9a-[2-[4-(dimethylamino)phenyl]ethenyl]-3-ethyl-9,9a-dihydro-9,9-dimethyloxazolo[3,2-a]indol-2(3H)-one; 7-chloro-9a-[2-[4-(dimethylamino)phenyl]ethenyl]-9,9a-dihydro-3,9,9-trimethyloxazolo[3,2-a]indol-2(3H)-one; 9a-[2-[4-(dibutylamino)phenyl]ethenyl]-9,9a-dihydro-9,9-dimethyloxazolo[3,2-a]indol-2(3H)-one; 9a-[2-[4-(dimethylamino)phenyl]ethenyl]-9,9a-dihydro-9-(2-hydroxyethyl)-9-methyloxazolo[3,2-a]indol-2(3H)-one; 9a-[2-[4-(dimethylamino)phenyl]-1-propenyl]-9,9a-dihydro-9,9-dimethyloxazolo[3,2-a]indol-2(3H)-one; 9,9a-dihydro-7,9,9-trimethyl-9a-[2-(4-nitrophenyl)-ethenyl]oxazolo[3,2-a] indol-2(3H)-one; N-[4-[2-(2,3-dihydro-9,9-dimethyl-2-oxooxazolo[3,2-a]indol-9a(9H)-yl)ethenyl]phenyl] acetamide; 9a-[2-[4-(dimethylamino)phenyl]ethenyl]-9,9a-dihydro-6-methoxy-9,9-dimethyloxazolo[3,2-a]indol-2 (3H)-one; 9a-[2-[4-(dimethylamino)phenyl]ethenyl]-2,3,9,9a-tetrahydro-9,9-dimethyl-2-oxooxazolol3,2-a]indole-7-carboxylic acid ethyl ester; 9a-[2-[4-(dimethylamino) phenyl]ethenyl]-9,9a-dihydro-7,9,9-trimethyloxazolo[3,2-a] indol-2(3H )-one; 10a-[2-[4-(dimethylamino)phenyl] ethenyl]-10a, 11-dihydro-11,11-dimethylbenz[e]oxazolo[3,2-a]indol-9(8H)-one; 9,9a-dihydro-9,9-dimethyl-9a-[2-(4-nitrophenyl)ethenyl]oxazolo[3,2-a]indol-2(3H)-one; 7-chloro-9a-[2-[4-(dimethylamino)phenyl]ethenyl]-9,9a-dihydro-9,9-dimethyloxazolo[3,2-a]indol-2(3H)-one; 9a-[2-[4-(dimethylamino)phenyl]ethenyl]-9,9a-dihydro-9,9-dimethyloxazolo[3,2-a]indol-2(3H)-one; 4-[2-(7-chloro-2,3-dihydro-9,9-dimethyloxazolo[3,2-a]indol-9a(9H)-yl) ethenyl]-N,N-dimethylbenzenamine; 4-[2-(2,3-dihydro-9,9-dimethyloxazolo[3,2-a]indol-9a(9H)-yl)ethenyl]-N,N- dimethylbenzenamine; 4-[2-(7-chloro-2,3-dihydro-2,9,9-trimethyloxazolo[3,2-a]indol-9a(9H)-yl)ethenyl]-N,N-dimethylbenzenamine; 4-[2-(2,3-dihydro-9,9-dimethyloxazolo[3,2-a]indol-9a(9H)-yl)-1-methylethenyl]-N,N-dimethylbenzenamine; 4-[2-(2,3-dihydro-9,9-dimethyloxazolo[3,2-a]indol-9a(9H)-yl)ethenyl]-N,N-diethylbenzenamine; 2,3,9,9a-tetrahydro-7-methoxy-9,9-dimethyl-9a-[2-(4-nitrophenyl)ethenyl]oxazolo[3,2-a]indole; 4-[2-(2,3-dihydro-9,9-dimethyl-7-nitrooxazolo[3,2-a]indol-9a(9H)-yl)ethenyl]-N,N-dimethylbenzenamine; N,N-dibutyl-4-[2-(2,3-dihydro-9,9-dimethyloxazolo[3,2-a]indol-9a(9H)-yl)ethenyl]benzenamine; 2,3,9,9a-tetrahydro-9,9-dimethyl-7-nitro-9a-[2-(4-nitrophenyl)ethenyl]oxazolo[3,2-a]indole; 7-chloro-2,3,9,9a-tetrahydro-9,9-dimethyl-9a-[2-(4-nitrophenyl)ethenyl]oxazolo[3,2-a]indole; 4-[2-(2,3-dihydro-7-iodo-9,9-dimethyloxazolo[3,2-a]indol-9a(9H)-yl)ethenyl]-N,N-dimethylbenzenamine; 4-[2-(2,3-dihydro-5-methoxy-9,9-dimethyloxazolo[3,2-a]indol-9a(9H)-yl)ethenyl]-N,N-dimethylbenzenamine; 4-[2-(2,3-dihydro-7-methoxy-9,9-dimethyloxazolo[3,2-a]indol-9a(9H)-yl)ethenyl]-N,N-dimethylbenzenamine; 4-[4-(2,3-dihydro-9,9-dimethyloxazolo[3,2-a]indol-9a(9H)-yl)-1,3-butadienyl]-N,N-diethylbenzenamine; 4-[4-(7-chloro-2,3-dihydro-9,9-dimethyloxazolo[3,2-a]indol-9a(9H)-yl)-1,3-butadienyl]-N,N-dimethylbenzenamine; 4-[4-(2,3-dihydro-9,9-dimethyloxazolo[3,2-a]indol-9a(9H)-yl)-1,3-butadienyl]-N,N-dimethylbenzenamine; 4-[4-(2,3-dihydro-7-methoxy-9,9-dimethyloxazolo[3,2-a]indol-9a(9H)-yl)-1,3-butadienyl]-N,N-dimethylbenzenamine; 2,3,9,9a-tetrahydro-7,9,9-trimethyl-9a-[2-(4-nitrophenyl)ethenyl]oxazolo[3,2-a]indole; N-[4-[2-(2,3-dihydro-9,9-dimethyloxazolo[3,2-a]indol-9a(9H)-yl)ethenyl]phenyl]acetamide; 4-[2-(2,3-dihydro-6-methoxy-9,9-dimethyloxazolo[3,2-a]indol-9a(9H)-yl)ethenyl]-N,N-dimethylbenzenamine; 4-[2-(8,9-dihydro-11,11-dimethylbenz[e]oxazolo[3,2-a]indol-10a(11H)-yl)ethenyl]-N,N-dimethylbenzenamine; 4-[2-(2,3-dihydro-7,9,9-trimethyloxazolo[3,2-a]indol-9a(9H)-yl)ethenyl]-N,N-dimethylbenzenamine; 2,3,9,9a-tetrahydro-9,9-dimethyl-9a-[2-(4-nitrophenyl)ethenyl]oxazolo[3,2-a]indole; 9,9a-dihydro-9,9-dimethyl-9a-[2-(9-methyl-9H-carbazol-3-yl)ethenyl]-7-(methylsulphonyl)oxazolo[3,2-a]indol-2(3H)-one; 9a-[2-(9-hexyl-9H-carbazol-3-yl)ethenyl]-2,3,9,9a-tetrahydro-9,9-dimethyl-7-(phenylsulphonyl)oxazolo[3,2-a]indole; 2,3,9,9a-tetrahydro-9,9-dimethyl-7-(methylsulphonyl)-9a-[2-(9-octyl-9H-carbazol-3-yl)ethenyl]oxazolo[3,2-a]indole; 9a-[2-(9-butyl-6-methoxy-9H-carbazol-3-yl)ethenyl]-2,3,9,9a-tetrahydro-9,9-dimethyloxazolo[3,2-a]indole-7-carboxylic acid ethyl ester; 9a-[2-(9-ethyl-9H-carbazol-3-yl)ethenyl]-2,3,9,9a-tetrahydro-9,9-dimethyloxazolo[3,2-a]indole-7-sulphonic acid methyl ester; 3-chloro-6-[2-[2,3-dihydro-9,9-dimethyl-7-(methylsulphonyl)oxazolo[3,2-a]indol-9a(9H)-yl]ethenyl]-9-octyl-9H-carbazole; 3-[2-[2,3-dihydro-9,9-dimethyl-7-(methylsulphonyl)oxazolo[3,2-a]indol-9a(9H)-yl]ethenyl]-9-methyl-9H-carbazole; 3-[2-[9-(2-ethoxyethyl)-2,3-dihydro-9-methyl-7-(methylsulphonyl)oxazolo[3,2-a]indol-9a(9H)-yl]ethenyl]-9H-carbazole; 9a-[2-(9-hexyl-9H-carbazol-3-yl)ethenyl]-2,3,9,9a-tetrahydro-9-(2-hydroxyethyl)-9-methyloxazolo[3,2-a]indole-7-carboxylic acid ethyl ester; 2,3,9,9a-tetrahydro-9,9-dimethyl-9a-[2-(9-octyl-9H-carbazol-3-yl)ethenyl]oxazolo[3,2]indole-7-carboxylic acid ethyl ester; 9a-[2-(9-butyl-9H-carbazol-3-yl)ethenyl]-2,3,9,9a-tetrahydro-9,9-dimethyloxazolo[3,2-a]indole-7-carboxylic acid ethyl ester; 2,3,9,9a-tetrahydro-9,9-dimethyl-9a-[2-(9-methyl-9H-carbazol-3-yl)ethenyl]oxazolo[3,2-a]indole-7-carboxylic acid ethyl ester; 9a-[2-(9-butyl-6-ethoxy-9H-carbazol-3-yl)ethenyl]-2,3,9,9a-tetrahydro-N,N,9,9-tetramethyloxazolo[3,2-a]indole-7-amine; 2,3,9,9a-tetrahydro-9-methyl-9a-[2-(9-methyl-9H-carbazol-3-yl)ethenyl]oxazolo[3,2-a]indole-9-ethanol; 9a-[2-(9-butyl-9H-carbazol-3-yl)ethenyl]-2,3,9,9a-tetrahydro-N,N,9,9-tetramethyloxazolo[3,2-a]indol-7-amine; 3-[2-(2,3-dihydro-6-methoxy-9,9-dimethyloxazolo[3,2-a]indol-9a(9H)-yl)ethenyl]-9-methyl-9H-carbazole; 3-[2-(2,3-dihydro-9,9-dimethyloxazolo[3,2-a]indol-9a(9H)-yl)-1-propenyl]-9-methyl-9H-carbazole; 3-[2-(7-chloro-2,3-dihydro-9,9-dimethyloxazolo[3,2-a]indol-9a(9H)-yl)-ethenyl]-9-methyl-9H-carbazole; 3-bromo-6-[2-(2,3-dihydro-9,9-dimethyloxazolo[3,2-a]indol-9a(9H)-yl]ethenyl]-9-ethyl-9H-carbazole; 3-[2-(2,3-dihydro-9,9-dimethyloxazolo[3,2-a]indol-9a(9H)-yl)ethenyl]-9-methyl-9H-carbazole.

17. The composition according to claim 16, wherein the at least one compound of formula (I) is chosen from the compounds presented in the table below:

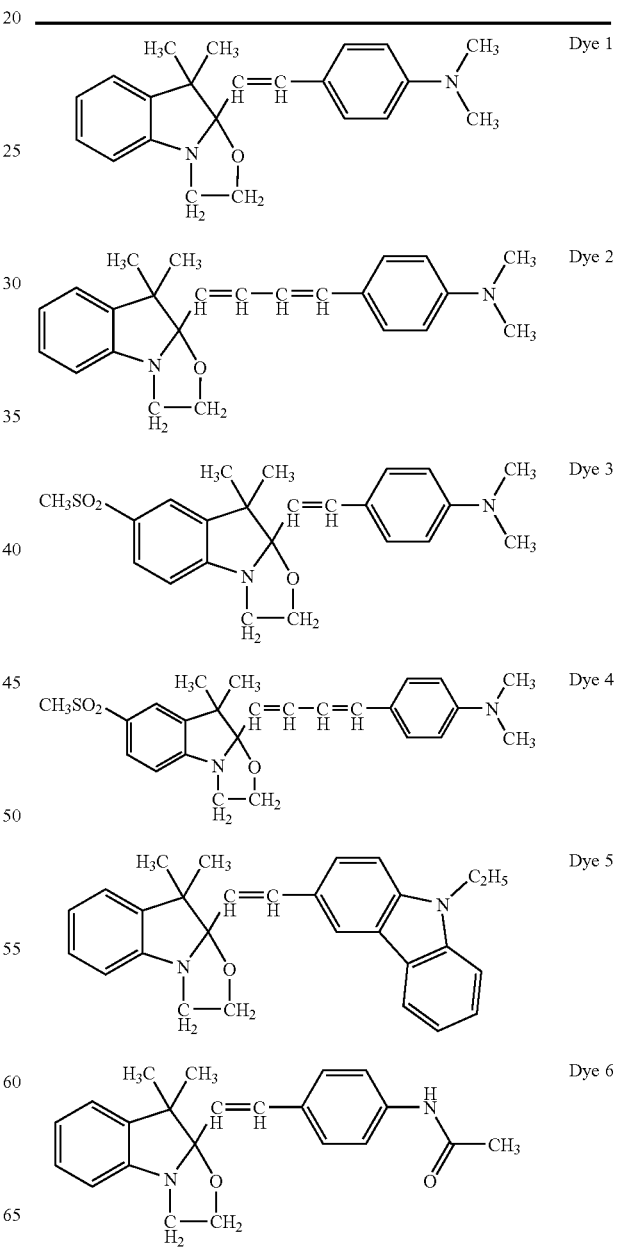

-continued

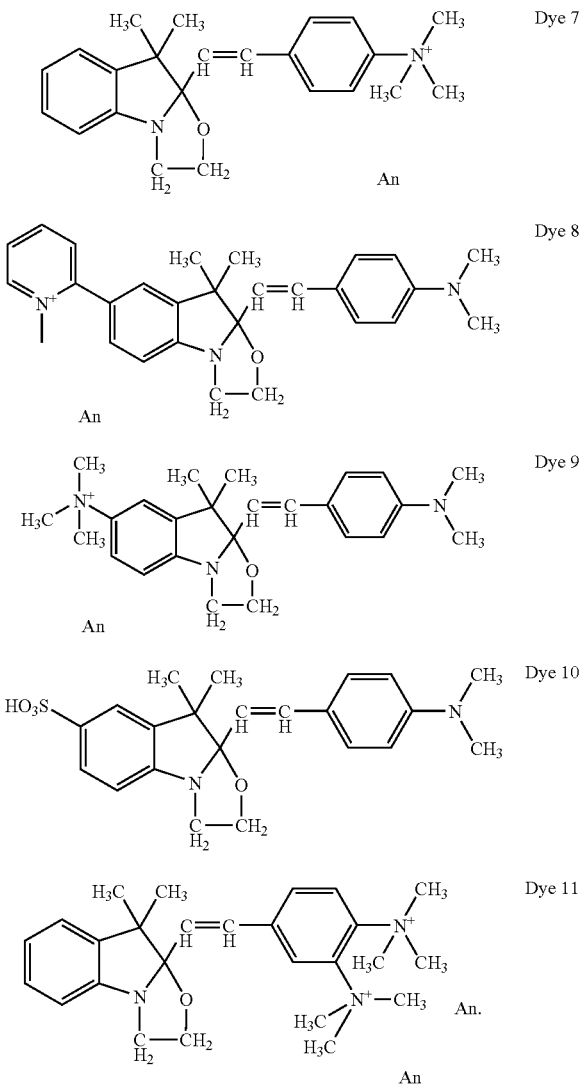

18. The composition according to claim 1, wherein the at least one compound of formula (I) is chosen from 3,3-dimethyl-2-(p-dimethylaminostyryl)-indolino[1,2-b]thiazoline; 3,3,5-trimethyl-2-(p-dimethylaminostyryl)indolino]1,2-b]thiazoline; 3,3,5-trimethyl-2-(p-chlorostyryl)indolino[1,2-b]thiazoline; 3,3,5-trimethyl-2-[2-(thienyl)vinyl]indolino[1,2-b]thiazoline; 3,3-dimethyl-5-methoxy-2-[2-(9-ethylcarbazolyl)vinyl]indolino[1,2-b]thiazoline; 3,3-dimethyl-5-carboethoxy-2-(p-dimethylaminostyryl)indolino[1,2-b]thiazoline; 3,3-dimethyl-5-chloro-2-[2-(benzothiazolyl)vinyl]indolino[1,2-b]thiazoline; 3,3-dimethyl-5-methoxy-2-(p-dimethylaminostyryl)indolino[1,2-b]thiazoline; 3,3-dimethyl-5-carboethoxy-2-(3,4-methylenedioxystyryl)indolino[1,2-b]thiazoline; 3,3-dimethyl-5-chloro-2-(p-methyl-styryl)indolino[1,2-b]thiazoline; 3,3-dimethyl-5-chloro-2-(p-methoxystyryl]indolino[1,2-bithiazoline; 3,3,5-trimethyl-2-(p-acetylaminostyryl)indolino[1,2-b]thiazoline; 3,3-dimethyl-5-methoxy-2-(3-hydroxy-4-methoxy-styryl)indolino[1,2-b]thiazoline; 3,3-dimethyl-5-carboethoxy-2-(o-cyanostyryl)-indolino[1,2-b]thiazoline; 3,3-dimethyl-5-chloro-2-(p-dimethylaminostyryl)-indolino[1,2-b]thiazoline; 3,3-dimethyl-5-methyl-sulphonyl-2-(p-dimethyl-aminostyryl)indolino[1,2-b]thiazoline; 3,3-dimethyl-5-phenylsulphonyl-2-(p-dimethylaminostyryl)indolino[1,2-b]thiazoline; 3,3-dimethyl-5-ethoxycarboxy-2-(p-dimethylaminostyryl)indolino[1,2-b]oxazoline.

19. The composition according to claim 1, wherein the at least one compound of formula (I), and the addition salts thereof, represents from 0.0001% to 30% by weight relative to the total weight of the composition.

20. The composition according to claim 1, wherein the at least one thiol compound is chosen from thioglycolic acid, thiolactic acid, mercaptopropionic acid, cysteamine, thiosuccinic acid, cysteine; acetylcysteine; glyceryl thioglycolate; thioglycerol, or their salts, alone or as mixtures.

21. The composition according to claim 20, wherein the at least one thiol compound is present in an amount ranging from 0.001% and 30% by weight relative to the total weight of the composition.

22. The composition according to claim 1, wherein the suitable dyeing medium is constituted of water or of at least one organic solvent or of a mixture of water and of at least one organic solvent.

23. The composition according to claim 1, wherein the pH is greater than the pKa of the compound of formula (I) and less than or equal to 12.

24. The composition according to claim 1, wherein the dye composition comprises at least one additive chosen from anionic, cationic, nonionic, amphoteric or zwitterionic surfactants or mixtures thereof, anionic, cationic, nonionic, amphoteric or zwitterionic polymers or mixtures thereof, inorganic or organic thickeners, antioxidants, penetrating agents, sequestrants, fragrances, buffers, dispersants, conditioning agents, preserving agents and opacifiers.

25. A process for treating keratin fibres, wherein the composition according to claim 1 is applied to said fibres for a sufficient leave-on time, this application being optionally followed by rinsing out.

26. The process according to claim 25, wherein a pre-treatment is performed through the action of a revealing agent such as acidifying agents and solvents or the combination of one or more of these revealing agents.

27. The process according to claim 25, wherein a post-treatment is performed through the action of a revealing agent such as light, an electrical current, heat, an acidifying agent, a solvent, an electromagnetic radiation or the combination of one or more of these revealing agents.

28. The process according to claim 25, wherein the dye composition is applied in the presence of at least one oxidizing agent.

29. A multicompartment device containing in a first compartment a dye composition as defined in claim 1 and in a second compartment at least one thiol compound as defined in claim 1.

30. The multicompartment device according to claim 29, containing, in a third compartment, at least one oxidizing agent.

31. The process for effacing the coloration obtained using a composition according to claim 1, wherein an effacing composition comprising at least one basifying agent is applied to said fibres, in a content such that the pH of the treated fibres is greater than the pKa of the compound(s) of formula (I) present in the composition giving rise to the coloration.

* * * * *

UNITED STATES PATENT AND TRADEMARK OFFICE
CERTIFICATE OF CORRECTION

PATENT NO.        : 7,585,332 B2
APPLICATION NO.   : 11/907622
DATED             : September 8, 2009
INVENTOR(S)       : Grégory Plos It is certified that error appears in the above-identified patent and that said Letters Patent is hereby corrected as shown below:

Claim 3, column 23, line 36, "phosphonyl($C_{1-6}$)alkyl" should read --phosphonyl($C_1$-$C_6$)alkyl--.

Claim 3, column 23, line 62, "(-$SO_3$)," should read --(-$SO_3^-$),--.

Claim 16, column 26, lines 34-35, "4-[2-(7-methoxy-9,9-dimethyloxazolol3,2-a]indol-9a(9H)-yl)ethenyl]-N,N-dimethylbenzenamine;" should read --4-[2-(7-methoxy-9,9-dimethyloxazolo[3,2-a]indol-9a(9H)-yl)ethenyl]-N,N-dimethylbenzenamine;--.

Claim 16, column 26, lines 53-55, "9a-[2-[4-(dimethylamino)phenyl]ethenyl]-2,3,9, 9a-tetrahydro-9,9-dimethyl-2-oxooxazolol3,2-a]indole-7-carboxylic" should read --9a-[2-[4-(dimethylamino)phenyl]ethenyl]-2,3,9,9a-tetrahydro-9,9-dimethyl-2-oxooxazolo[3,2-a]indole-7-carboxylic--.

Claim 18, column 29, lines 50-51, "3,3,5-trimethyl-2-(p-dimethylaminostyryl)-indolino]1,2-b]thiazoline;" should read --3,3,5-trimethyl-2-(p-dimethylaminostyryl)-indolino[1,2-b]thiazoline;--.

Signed and Sealed this

Eighth Day of December, 2009

David J. Kappos
*Director of the United States Patent and Trademark Office*